United States Patent
Witiak et al.

(10) Patent No.: US 6,531,499 B2
(45) Date of Patent: Mar. 11, 2003

(54) MATRIX METALLOPROTEINASE INHIBITORS AND METHOD OF USING SAME

(75) Inventors: Donald T. Witiak, deceased, late of Mount Vernon, OH (US), by Deanne B. Witiak, executor; Paul J. Bertics, Oregon, WI (US); Yingsheng Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/911,014

(22) Filed: Jul. 23, 2001

(65) Prior Publication Data

US 2002/0032347 A1 Mar. 14, 2002

Related U.S. Application Data

(62) Division of application No. 09/326,033, filed on Jun. 4, 1999, now Pat. No. 6,294,694.

(51) Int. Cl.[7] .................. A01N 43/52; A61K 31/415
(52) U.S. Cl. .................. 514/389; 514/391; 514/595; 514/596; 514/597; 562/575; 564/47; 564/48; 564/52; 564/57; 564/58; 564/59; 564/60; 564/117; 564/118
(58) Field of Search ............... 514/389, 391, 514/595, 596, 594; 564/59, 60, 118, 117, 47, 48, 52, 57, 58; 562/575

(56) References Cited

U.S. PATENT DOCUMENTS

| | | | |
|---|---|---|---|
| 3,452,041 A | 6/1969 | Bell et al. | |
| 3,808,262 A | 4/1974 | Bernd et al. | |
| 4,235,885 A | 11/1980 | Sundeen et al. | |
| 4,263,293 A | 4/1981 | Sundeen et al. | |
| 4,276,284 A | 6/1981 | Brown | |
| 4,297,275 A | 10/1981 | Sundeen et al. | |
| 4,367,233 A | 1/1983 | Clark | |
| 4,371,465 A | 2/1983 | McGregor | |
| 4,371,466 A | 2/1983 | McGregor | |
| 4,374,765 A | 2/1983 | McGregor | |
| 4,382,081 A | 5/1983 | Sundeen et al. | |
| 4,588,034 A | 5/1986 | Galardy et al. | |
| 4,633,014 A | 12/1986 | Bremanis et al. | |
| 4,704,383 A | 11/1987 | McNamara et al. | |
| 4,950,755 A | 8/1990 | Witiak et al. | |
| 4,992,537 A | 2/1991 | Goldberg et al. | |
| 5,270,447 A | 12/1993 | Liotta et al. | |
| 5,866,570 A | 2/1999 | Liang et al. | |

FOREIGN PATENT DOCUMENTS

GB        1329491        9/1973

OTHER PUBLICATIONS

Boone, T.C. et al., cDNA Cloning and Expressioni of a Metalloproteinase Inhibitor Related to Tissue Inhibitor of Metalloproteinases, *Proc. Natl. Acad. Sci.* 87:2800.

(List continued on next page.)

*Primary Examiner*—T. D. Wessendorf
(74) *Attorney, Agent, or Firm*—Joseph T. Leone, Esq.; DeWitt Ross & Stevens S.C.

(57) ABSTRACT

Peptoid compounds of Formula I and Formula II are disclosed

The compounds are useful in the treatment of matrix metalloproteinase-mediated disorders.

23 Claims, 14 Drawing Sheets-

OTHER PUBLICATIONS

Carmichael, D.F. et al., Primary Structure and cDNA Cloning of Human Fibroblast Collagenase Inhibitor, *Proc. Natl. Acad. Sci.*, 83 2407.

Dayer, J.M. et al., Human Recombinant Interleukin 1 Stimulates Collagenase and Prostaglandin $E_2$ Production by Human Synovial Cells, *J. Clin. Inves.*, 77:645.

Dayer, J.M. et al., Cachetin/Tumor Necrosis Factor Stimulates Collagenase and Prostaglandin $E_2$ Production by Human Synovial Cells and Dermal Fibroblasts, *J. Exp. Med.*, 162:2163.

DeClerck, Y.A. e t al., Purification and Characterization of Two Related by Distinct Metalloproteinases Inhibitors Secreted by Bovine Aortic Endothelial Cells, *J. Biol. Chem.*, 264:17445.

Docherty, A.J.P. et al., Sequence of Human Tissue Inhibitor of Metalloproteinases and its Identity to Erythoid–Potentiating Activity, *Nature*, 318:66.

Gilchrist et al., "Reactive Intermediates. Part XXVI. Flash Pyrolysis of Phenyl–Substituted 1,2,4–Triazoles; A new Synthesis of Isoindoles," *J. Chem. Soc.*, Perkin Trans. 1, (1), 12–18.

Jentgens et al., *Helvetica Chim. Acta.*, 1997, vol. 80, 996–978.

Nowick et al., *J. Org. Chem.*, 1992, 57:3763–3765.

Welgus, H.G. et al., Neutral Metalloproteinases Produced by Human Mononuclear Phagocytes, *J. Clin. Invest.*, 86:1496.

Effects of Varying Concentrations of Compound 115.5.1 on MMP2 Collagenase Activity Effects of Varying Concentrations of Compound 115.5.1 on 3T3-F442A Fibroblast Viability Effects of Varying Concentrations of Compound 149.4.2 on MMP2 Collagenase Activity Effects of Varying Concentrations of Compound 149.4.2 on 3T3-F442A Fibroblast Viability

Effects of Varying Concentrations of Compound 69.3 on MMP2 Collagenase Activity Effects of Varying Concentrations of Compound 113.2 on MMP2 Collagenase Activity

Effects of TIMP-1 and Compound 113.2 on HiMel Cell Matrigel Invasion

MATRIX METALLOPROTEINASE INHIBITORS AND METHOD OF USING SAME

This is a divisional of application Ser. No. 09/326,033, filed Jun. 4, 1999, now U.S. Pat. No. 6,294,694.

This invention was made with United States government support awarded by the following agencies: NIH Grant No. AI3489 1. The United States has certain rights in this invention.

FIELD OF THE INVENTION

The invention is directed to novel matrix metalloproteinase inhibitors and their use in the treatment of matrix metalloproteinase-mediated disease states. The invention is further directed to combinatorial libraries of the compounds and methods to generate these libraries.

DESCRIPTION OF THE PRIOR ART

Matrix metalloproteinases, hereinafter referred to as "MMP's," are a class of proteases which are capable of degrading basement membranes and/or collagen. MMP's are often also referred to using more specific names, such as collagenases or gelatinases. Unless designated otherwise, the term MMP shall refer to all enzymes which can be classified as matrix metalloproteinases.

The presence of circulating MMP's is associated with a host of disease states, including endotoxic shock, systemic inflammatory response syndrome (SIRS), metastatic and/or invasive cancer, malaria, as well as the presence of other pathogenic organisms. Elevated MMP levels have also been associated with autoimmune diseases such as arthritis. The appearance of elevated MMP concentrations in a mammal is frequently followed by death of the subject due to vascular leakage (i.e., the leakage of plasma proteins into the tissues) and/or SIRS leading to multiple organ failure. SIRS, as befitting its designation as a "syndrome," is etiologically linked to a host of conditions often leading to fatal consequences, including sepsis syndrome, non-responsive septic shock, multiple organ failure syndrome, immuno-mediated organ injury, pancreatitis, hemorrhage, ischemia, or multiple trauma. Where the precipitating condition is an acute occurence, such as ischemia or multiple trauma, the rise in MMP levels can be extremely rapid and if not quickly stabilized and lowered will cause death. Where the precipitating condition tends toward a more chronic ailment, such as a slowly invading malignancy, the rise in MMP levels tends to mirror the growth pattern of the tumor.

Individual matrix metalloproteinases within the larger class of MMP enzymes are designated numerically. Of particular interest are MMP-2 and MMP-9. These two MMP's have been clearly and positively correlated to the presence of invasive and/or metastatic cancer, as well as to certain immune system dysfunctions, as noted hereinabove. MMP-2 and MMP-9 fall within a sub-class of MMPs designated "Type IV" collagenases. Type IV collagenases like MMP-2 and MMP-9 are known to be involved in the breakdown of Type IV collagen, a major component of basement membrane (20 to 70% by total mass). See U.S. Pat. No. 5,866,570, to Liang et al. In mammals, Type IV collagen defines a supramolecular network which maintains the integrity of the basement membrane. Consequently, degradation of Type IV collagen by MMP-2 and MMP-9 is believed to be a critical step in basement membrane degradation. The complete amino acid sequences for both MMP-2 and MMP-9 are known, as are the sequences for the their respective and inactive pre-pro and pro-forms. See U.S. Pat. No. 4,992,537 to Goldberg et al. MMP-2 and MMP-9 can be purchased from several international suppliers, including Sigma, St. Louis, Mo.

Several synthetic MMP inhibitors have been described in the patent literature. For instance, U.S. Pat. No. 5,866,570, to Liang et al., noted above, describes bis(dioxopiperazine) compounds which are potent MMP inhibitors. For descriptions of others compounds and treatments which have been reported as having MMP-inhibitory activity, see U.S. Pat. Nos. 4,235,885; 4,263,293; 4,276,284; 4,297,275; 4,367,233; 4,371,465; 4,371,466; 4,374,765; 4,382,081; 4,558,034; 4,704,383; 4,950,755; and 5,270,447. All of these compounds suffer from certain intractable drawbacks, such as cytoxicity or difficult syntheses, which have limited their in vivo application as MMP inhibitors.

There are also known at least two endogenous MMP inhibitors known as tissue inhibitors of metalloproteinase (TIMP's): TIMP-1 and TIMP-2. The complete amino acid sequences for these proteinaceous MMP inhibitors are known. See DeClerk et al. (1989) *J. Biol. Chem.* 264:17445; Boone et al. (1990) *Proc. Natl. Acad. Sci. USA* 87:2800; Docherty et al. (1985) *Nature* 318:65; and Carmichael et al. (1986) *Proc. Natl. Acad. Sci. USA* 83:2407.

The expression of MMP's in general and collagenases in particular has been studied by several research groups. For instance, Wegus and co-workers have shown that mononuclear phagocytes secrete several different MMP's, including a 57 kD interstitial collagenase (MMP-1), a 72 kD Type IV collagenase (MMP-2), a 60 kD stromelysin (MMP-3), and a 92 kD Type IV collagenase (MMP-9). This same group has also shown that endotoxin stimulates the secretion of MMP-1, MMP-2, MMP-3, and MMP4 from mononuclear phagocytes in vitro. See Wegus et al. (1990) *J. Clin. Invest.* 86:1496.

Mononuclear phagocytes are also known to secrete interleukin-1 and tumor necrosis factor, compounds which induce MMP gene expression. See Dayer et al. *J. Clin. Invest.* (1986) 77:645 and Dayer et al. (1985) *J. Exp. Med.* 162:2163.

Currently, sepsis, septic shock, and the like are treated symptomatically by supporting respiration, replacing lost blood volume, and administering vasoactive drugs to increase renal and/or cardiac function. Surgery and/or antibiotics are used to remove or kill infectious or malignant agents underlying the condition. However, there remains a long-felt need for effective, non-toxic medicinal compounds which are specific and potent inhibitors of MMP's.

SUMMARY OF THE INVENTION

A first embodiment of the invention is directed to compounds of Formula I or II:

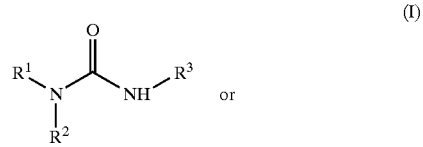

-continued (II)

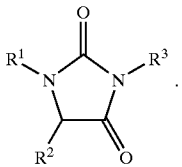

wherein $R^1$ is selected from the group consisting of H, $C_{1-12}$-alkyl, $C_{3-8}$-cycloalkyl, $C_{3-8}$-cycloalkyl-$C_{1-12}$-alkyl, amino-$C_{1-12}$-alkyl, N—$C_{1-6}$-alkylamino-$C_{1-12}$-alkyl, N,N-di-$C_{1-6}$-alkylamino-$C_{1-12}$-alkyl,

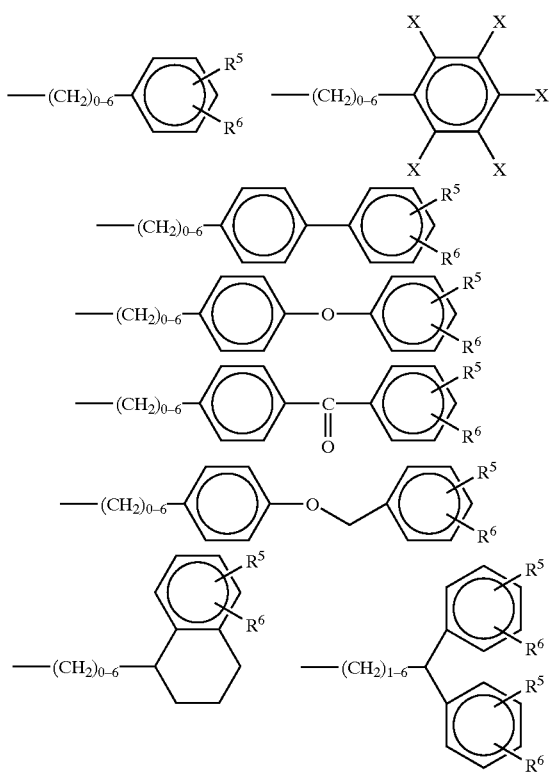

and

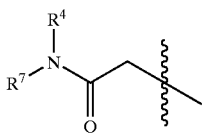

wherein $R^5$ and $R^6$ are independently selected from the group consisting of H, $C_{1-6}$-alkyl, $C_{1-6}$-alylthio, $C_{1-6}$-alkoxy, fluoro, chloro, bromo, iodo, and nitro; and X is halo;

wherein $R^4$ is selected from the group recited above for $R^1$, and $R^7$ is selected from the group consisting of

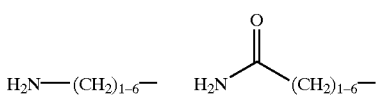

-continued

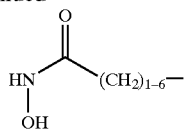

$R^2$ and $R^3$ are selected from the group consisting of

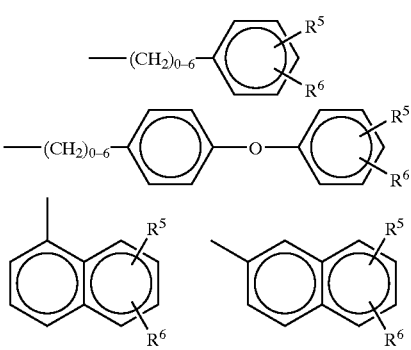

wherein $R^5$ and $R^6$ are as described above; and pharmaceutically-suitable salts thereof.

A second embodiment of the invention is directed to solution-phase or resin-bound combinatorial libraries containing any combination of the above-described compounds.

A third embodiment of the present invention is drawn to pharmaceutical compositions for the treatment of MMP-mediated diseases in mammals. The composition includes an amount of one or more of the above-described compounds in an amount effective to inhibit MMP activity, optionally in combination with a pharmaceutically-acceptable carrier. The pharmaceutical composition is effective to inhibit and to treat disorders in which MMP activity plays a role, including endotoxic shock, SIRS, invasive cancers, and metastatic cancers.

A fourth embodiment of the invention is directed to a method of inhibiting or treating MMP-mediated diseases in mammals, including human. The invention thus provides a method of treating a host mammal afflicted with an MMP-mediated disorder, the method comprising administering to the mammal an effective MMP-inhibitory amount of a compound of Formula I or II or a pharmaceutically-acceptable salt thereof, optionally in combination with a pharmaceutically-acceptable carrier. The invention further provides a method of inhibiting and/or preventing MMP-mediated disorders, including invasive and metastatic carcinomas, endotoxic shock, and SIRS, the method comprising administering to a mammal susceptible of developing an MMP-mediated disorder an effective MMP-inhibitory amount of a compound of Formula I or II or a pharmaceutically-acceptable salt thereof, optionally in combination with a pharmaceutically-acceptable carrier.

It has now been found that the subject compounds, including pharmacologically-active isomers and pharmaceutically-acceptable salts thereof, possess potent MMP inhibitory activities. Accordingly, they are useful in the treatment of disease conditions wherein MMP activity is a contributing factor. Most notably, the subject compounds are useful in the treatment of endotoxic shock,(SIRS, multiple organ failure syndrome, and metastatic and invasive cancers.

The subject compounds are also notable in that while they possess potent MMP inhibitory activity, they also have low cytotoxicity and do not inhibit fibroblast motility.

Consequently, the compounds can be administered in relatively large concentrations to maximize the benefit of their MMP inhibitory activity, without encountering adverse cytotoxic side effects.

The invention also discloses solid-phase synthetic methodologies to construct diversified combinatorial libraries of the subject peptoid/urea compounds. Detailed herein is a convergent, solid-phase method to synthesize these libraries. Each library contains approximately 100 compounds of known structure and equivalent molarity. A high throughput gelatinase assay can be used to screen and select library members having maximum activity to inhibit gelatinase. A deconvolution technique is also described to target those compounds having the greatest inhibitory activity; these compounds are then resynthesized individually and further characterized or advanced to human clinical trials.

The MMP inhibitors disclosed herein provide novel agents for cancer chemotherapy, especially for treating highly malignant and metastatic tumors.

Further aims, objects, and advantages of the present invention will become apparent upon a complete reading of the Detailed Description which follows.

DETAILED DESCRIPTION OF THE INVENTION

Figure 1:
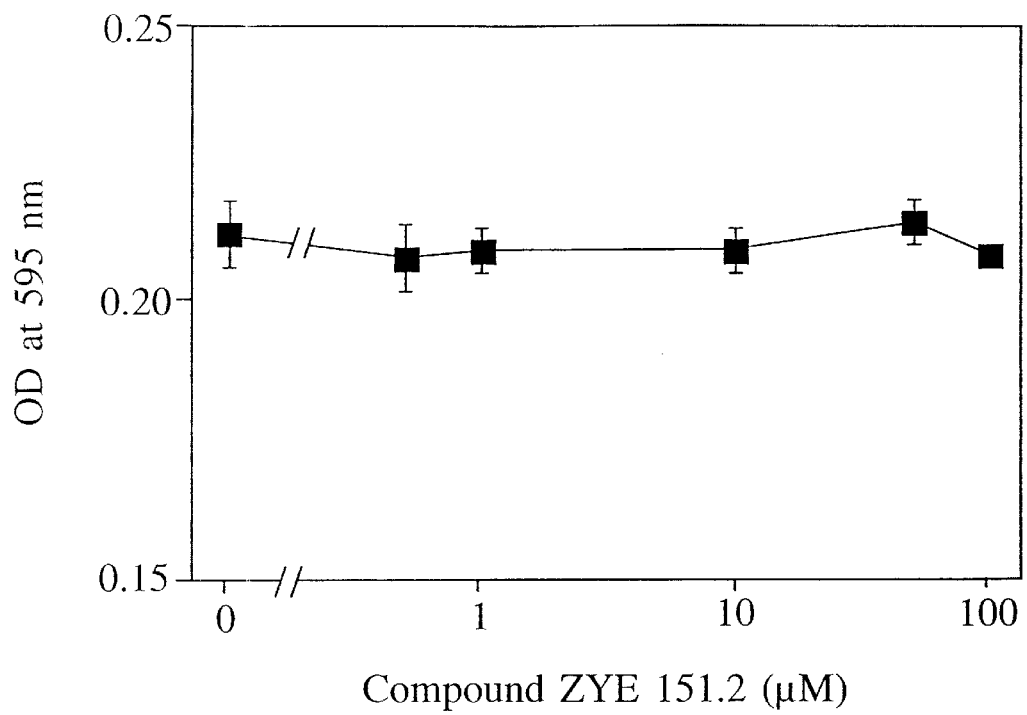
FIG. 1 is a graph depicting the in vitro effect of a subset of the subject compounds on F442A fibroblast (a murine fibroblast cell line) viability. See Example 1.
Figure 1:
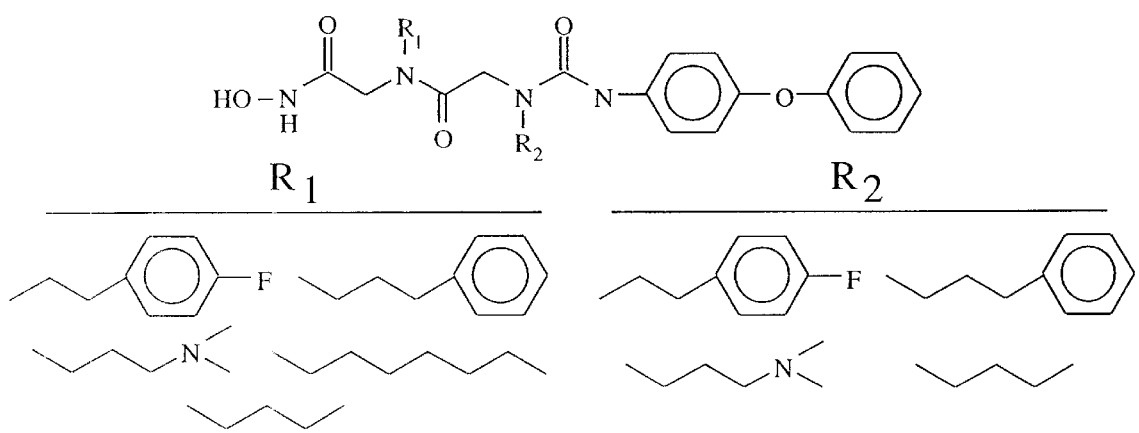

The invention is specifically drawn to the above-recited compounds and the use of the compounds in the treatment of MMP-mediated diseases. In particular, the invention is directed to use of these compounds to prevent and treat invasive cancers and to inhibit or otherwise treat metastatic cancers. The invention is also drawn to use of these compounds to treat endotoxic shock and SIRS. The compounds may be used to treat humans.

The compounds of the present invention may exist in isomeric forms within the various R groups. For example, if the compounds have an asymmetric carbon within one or more of the R groups, they can exist in the form of different combinations of R and S isomeric forms as enantiomers, diastereomers or racemates.

In addition cis- and trans-geometric isomers may also be present in the subject compounds due to cis- and trans-configurations inherent within any double bonds present in the substituents. Therefore, by starting with an appropriate cis- or trans-precursor, the corresponding end product of Formula I or II will be obtained.

All racemic and isomeric forms of the compounds of Formulas I and II, including pure enantiomeric, diastereomeric and geometric isomers and mixtures thereof, are within the scope of this invention. Unless otherwise specified, the compounds of the hereinafter examples are in racemic form.

The invention also comprehends salts of the compounds. These salts include acid addition salts such as those made from inorganic acids such as hydrochloric acid, nitric acid, and the like, or from organic acids such as citric acid, lactic acid and the like. The salts also include these made with bases, such as sodium and potassium hydroxide. The salts of the invention are made by conventional methods well known to those skilled in the art. The salts for therapeutic use of the subject compounds are pharmaceutically-acceptable salts, as are well understood in the art.

Abbreviations and Definitions

The following abbreviations are used throughout the specification and claims. Unless specifically defined to the contrary, all other terms have their standard accepted meanings. All of the following compounds can be purchased commercially from Aldrich Chemical Company, Milwaukee, Wis., USA, as well as other national and international suppliers:

"alkyl"=a straight or branched saturated hydrocarbon substituent

"BSA"=bovine serum albumin

"DCM"=dichloromethane

"DEAD"=diethyl azodicarboxylate

"DIC"=diisopropylcarbodiimide

"DIEA"=diisopropylethyl amine

"DMAP"=4-dimethylaminopyridine

"DMEM"=Dulbecco's modified Eagle medium

"DMF"=dimethylformamide

"DMSO"=dimethylsulfoxide

"BOP"=bis(2-oxo-3-oxazolidinyl) phosphonic acid

"DTNB"=Ellman's reagent: 5,5'-dithio-bis(2-nitrobenzoic acid)

"Fmoc"=9-fluorenylmethyl chloroformate

"HEPES"=N-2-hydroxyethylpiperazine-N'-2-ethanesulfonic acid

"THF"=tetrahydrofuran

"PPh$_3$"=triphenylphosphine

"SIRS"=systemic inflammatory response syndrome

"TFA"=trifluoroacetic acid
"Triphosgene"=bis(trichloromethyl) carbonate
"Trityl"=triphenylmethyl
"Wang's resin"=4-benzyloxybenzyl alcohol, bonded to polystyrene beads (Aldrich Chemical Co. catalog no. 47,703-6)

Chemistry

The compounds of the present invention are prepared by the synthetic procedures outlined in the following Reaction Schemes. Work up and deconvolution of the combinatorial libraries constructed as detailed below may be advantageously carried out if necessary by standard and well-known methodologies. Insofar as certain approaches to produce and deconvolute combinatorial libraries are well-known and form no part of the present invention, they will not be described in great detail. Several recent reviews are available; see, for instance, Ellman (1996) *Acc. Chem. Res.* 29:132–143 and Lam et al. (1997) *Chem. Rev.* 97:411–448.

Intermediate products obtained may be quite suitable without further purification for the preparation of the final products, which then may be purified. Purification is readily achieved by conventional methods in the art, for example, by recrystallization techniques, chromatography, and the like.

With reference to Schemes 1 and 2, compounds having the following structures can be made:

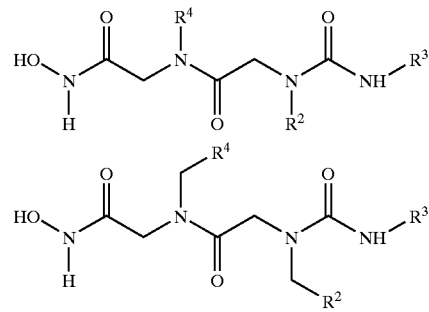

Scheme 1

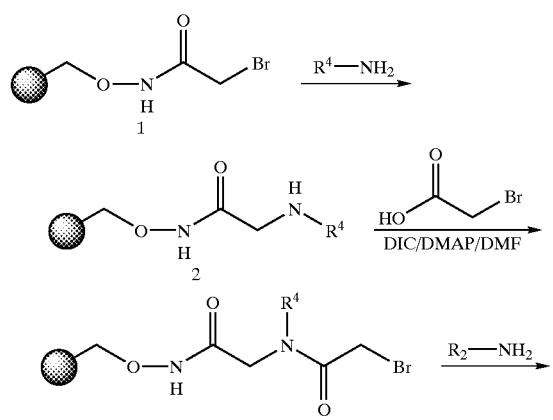

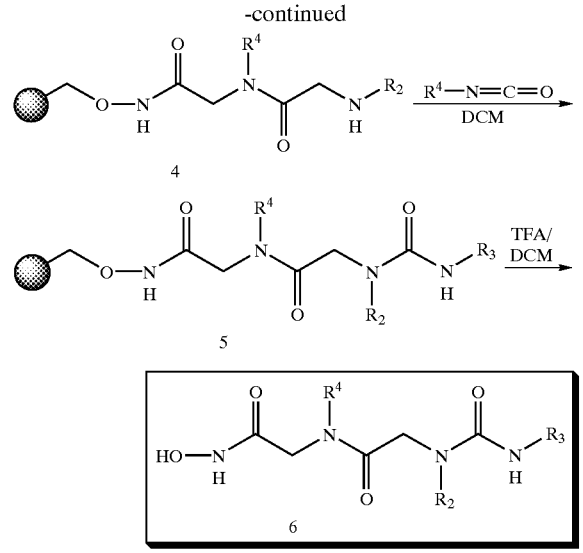

Scheme 2

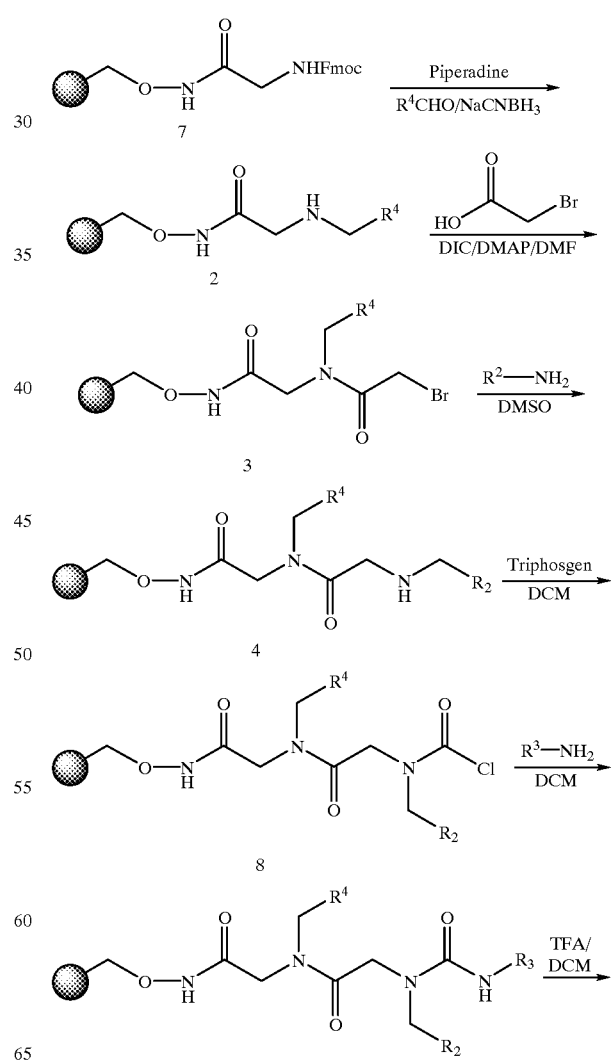

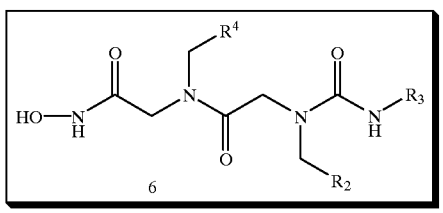

Synthesis of 1: Wang's hydroxylamine resin (see below for synthesis) (1 equ) is swelled in DMF and α-bromo acetic acid (5 equ) and DIC (6 equ) are added thereto. The resulting suspension is stirred at room temperature for 5 minutes, and then 100 mM DMAP in DMF (0.5 equ) is added dropwise. The suspension is then stirred overnight, filtered, and washed sequentially with DMF, DCM, methanol and dried under vacuum to provide the yellow-colored resin 1.

Synthesis of 2: Method A: Resin-bound 1 (1 equ) is swelled in anhydrous DMSO and an amine bearing the desired substituent $R^4$ (20 equ) is added. The suspension is stirred at room temperature overnight, filtered, and washed to give resin-bound 2. Method B: Resin-bound 7 (1 equ, see Scheme 2) is stirred in excess 40% piperidine in DMF for 30 minutes, and the suspension is then filtered, washed sequentially with DMF, DCM, and methanol and dried under vacuum. The dried resin is suspended in anhydrous DMF. The resulting suspension is treated with the appropriate aldehyde (10 equ), $NaCNBH_3$ (10 equ) and acetic acid (1%). When testing with ninhydrin shows the reaction is completed, the resin is filtered, washed with DMF, DCM, and methanol and dried to give resin-bound 2.

Synthesis of 3: Resin-bound 2 (1 equ) is swelled in DMF and a-bromo acetic acid (10 equ) and DIC (11 equ) are added thereto. The resulting suspension is stirred at room temperature for 5 minutes and then 100 mM DMAP (0.5 equ) is added dropwise. The suspension is then stirred overnight. If a bromophenol blue test is positive after stirring overnight, the above procedure is repeated. If the bromophenol blue test is negative, the resin is filtered and washed sequentially with DMF, DCM, methanol, and dried under vacuum to afford resin-bound 3.

Synthesis of 4: Resin-bound 3 (1 equ) is swelled in anhydrous DMSO and the appropriate amine (20 equ) is added. The suspension is stirred at room temperature overnight, filtered, and worked-up as previously described. Resin-bound 4 is afforded.

Synthesis of 5: Method A: Resin-bound 4 (I equ) is swelled in anhydrous DCM under argon and then an appropriate isocyanate (10 equ) is added via syringe. The resulting mixture is stirred at room temperature overnight, and then filtered, washed sequentially with DMF, DCM, methanol, and dried under vacuum to afford resin-bound 5. Method B: The dried resin-bound 8 (see Scheme 2) is swelled in anhydrous DCM, an appropriate amine is added thereto, and the reaction is run overnight under argon at room temperature. The work-up procedure is the same as described for Method A, thereby providing resin-bound 5.

Synthesis of 6: To cleave resin-bound 5 to yield free 6, resin-bound 5 is stirred with TFA/DCM (1:1) for 30 minutes and then filtered and washed with DCM. The combined filtrate is evaporated under vacuum and purified by HPLC to provide pure 6.

For 2-chloro-trityl resin: The resin 5 is stirred with 5% TFA in DCM for 30 minutes, filtered, and washed with DCM. The combined filtrate is evaporated under vacuum and purified by HPLC to afford 6.

Synthesis of 7: Hydroxylamine resin (1 equ) is swelled in DMF and Fmoc-gly-OH (5 equ), BOP (6 equ) and DIEA (6 equ) are added thereto. The resulting suspension is stirred at room temperature. Bromophenol blue testing generally indicates that the reaction is completed after 5 hours. The resulting resin is then filtered and washed sequentially with DMF, DCM, methanol and dried under vacuum to provide resin 7.

Synthesis 8: Resin 4 is swelled in anhydrous DCM and then triphosgen is added portion by portion under argon at 0° C. (caution: extremely exothermic). The resulting mixture is stirred vigorously at room temperature for 3 hours, and then filtered, washed sequentially with DMF and DCM, and dried under vacuum to provide the acyl chloride resin 8.

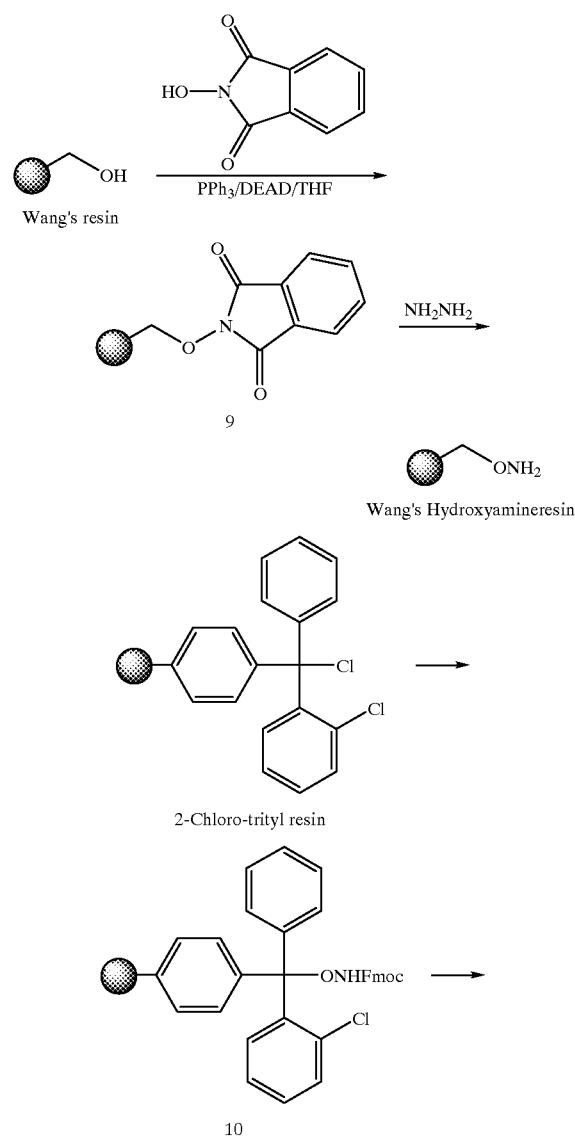

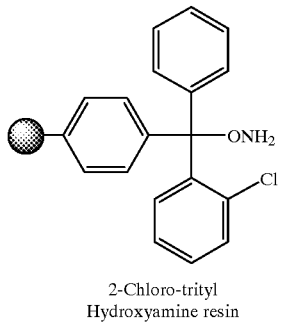

2-Chloro-trityl
Hydroxyamine resin

Referring now to Scheme 3, this Scheme illustrates the synthesis of Wang's hydroxyamine resin, Wang's 2-chloro-trityl resin, and Wang's 2-chloro-trityl-hydroxyamine resin:

Synthesis of Wang's hydroxyamine resin: Wang's resin is swelled in anhydrous THF, and then N-hydroxyphthalimide and triphenylphosphine (Ph$_3$P) is added thereto. The resulting suspension is vigorously stirred at room temperature until all the materials are dissolved. DEAD is added dropwise under argon and the reaction run for 20 hours. The resultant resin is filtered, washed sequentially with DMF, DCM, and methanol, and then dried under vacuum to provide resin 9. Dried resin 9 is stirred in THF/ethanol (1:2) at 0° C. for 1 hour, and then anhydrous hydrazine (6 equ) is added dropwise. The resulting suspension is stirred at room temperature for 17 hours and washed extensively with DMF, and then DCM, and then methanol to provide Wang's hydroxyamine resin.

Synthesis of 2-chloro-trityl hydroxyamine resin: 2-Chloro-trityl resin is gently stirred in DCM at room temperature and DIEA and N-Fmoc-hydroxylamine are added sequentially thereto. The resulting suspension is stirred gently for 48 hours, filtered, and sequentially washed with DMF, DCM, and methanol to provide resin 10. The dried resin 10 is stirred with 40% piperidine in DMF at room temperature for 30 minutes, filtered, and then sequentially washed with DMF, DCM, and methanol to provide 2-chloro-trityl hydroxyamine resin.

With reference to Schemes 4 and 5, compounds having the following structure can be made:

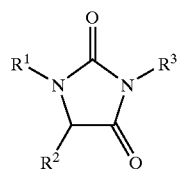

Scheme 4

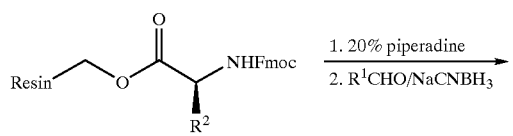

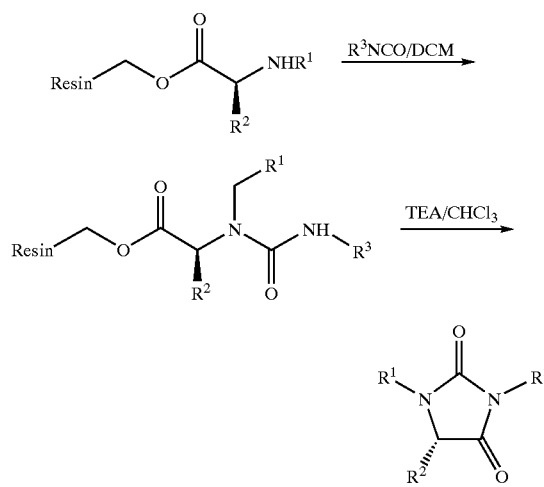

Wang's resin bound N-Fmoc amino acid is stirred at room temperature in 20% piperidine in DMF for 30 minutes. The resin is filtered and washed thoroughly with DMF. The resultant resin is swelled in DMF, and aldehyde, and then NaCNBH$_3$ are added. The reaction is allowed to run 24 hours and the resin is filtered off, washed with DMF, DCM, and MeOH and dried under vacuum. The dried resin is swelled in anhydrous DCM and an appropriate isocyanate is added. The resulting suspension is then stirred at room temperature overnight. The resin is filtered and washed as described immediately above. The resulting resin is suspended in anhydrous chloroform and refluxed 20 hr. Then the resin is filtered and washed with DCM. Combining the filtrate together and removing the solvent yields a solid product which may be further purified using HPLC.

Scheme 5

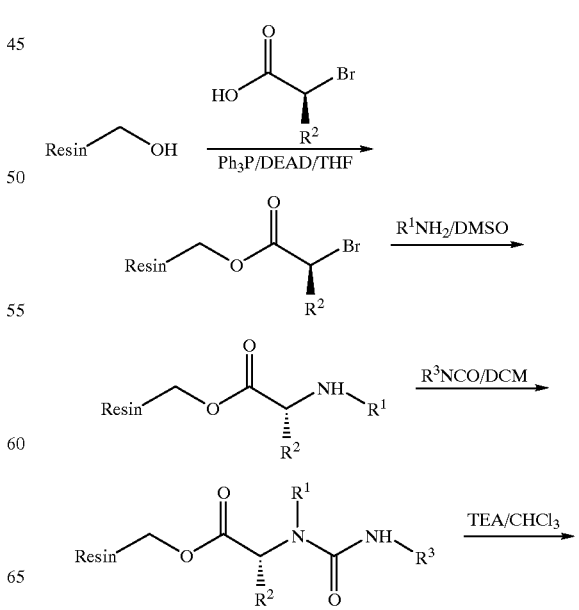

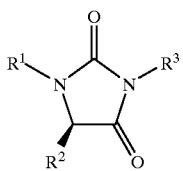

Wang's resin is suspended in THF and Ph₃P and and an R²-bromoacid are added. The suspension is then cooled to 0° C. and DEAD is added dropwise. The reaction mixture is stirred at 0° C. overnight and the resin is filtered and washed sequentially with DMF, DCM, and MeOH, and then dried. The dried resin is swelled in DMSO and an R¹-amine is added. The resulting suspension is stirred at room temperature for 24 hours and the resin is filtered off and washed as described above. The dried resin is swelled in anhydrous DCM and an R³-isocyanate is added. The resulting suspension is then stirred at room temperature overnight. The resin is filtered and washed as above. The resulting resin is suspended in anhydrous chloroform and refluxed 20 hours. The resin is then filtered and washed with DCM. The filtrates are combined and the solvent removed to yield the product as a solid. The product may be further purified using HPLC.

With reference to Scheme 6, compounds having the following structure can be made:

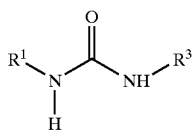

Scheme 6

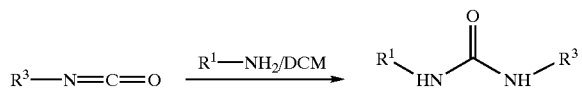

Here, an isocyanate bearing the R³ moiety is dissolved in anhydrous DCM and then an appropriate amine is added. The solution is stirred at room temperature overnight and the solvent removed. Dissolving the resultant solid in chloroform and washing with 1 N hydrochloric acid provides the pure product as a solid.

Combinatorial Chemistry

The defined peptoid structure of the compounds described herein makes these polyamide compounds highly useful for constructing large libraries of potentially useful compounds via combinatorial chemistry. Combinatorial exploration of functionalized oligomers of Formula I or II has a potential yield of literally millions of novel peptoid molecules.

The residues which comprise the finished peptoids can be functionalized prior to being incorporated into a final compound, or an unfunctionalized peptoid can be constructed and then the entire oligomer functionalized. Neither method is preferred over the other because they are complementary depending upon the types of compounds which are desired.

Combinatorial libraries utilizing the present compounds may be constructed using any means now known to the art or developed in the future. The preferred methods, however, are the "split and pool" method using solid-phase synthesis analogous to that used for polypeptide synthesis on inert solid substrates and parallel synthesis, also referred to as multipin synthesis.

The "split and pool" concept is based on the fact that combinatorial bead libraries contain single beads which display only one type of compound, although there may be up to $10^{13}$ copies of the same compound on a single 100 μm diameter bead. The process proceeds as follows, utilizing the reaction schemes described above:

Several suitable solid substrates are available commercially. The substrates are generally small diameter beads, e.g. about 100 μm, formed from inert polymeric materials such as polyoxyethylene-grafted polystyrene or polydimethylacrylamide. An illustrative substrate, marketed under the trademark "ARGOGEL" is available from Argonaut Technologies, Washington, D.C.

Referring now to FIG. 14, which is a schematic depicting the split and pool method, a plurality of inert substrates are divided into two or more groups and then a first set of subunits is covalently linked to the inert support. As depicted in FIG. 14, the initial plurality of substrates is divided into three subgroups. The appearance of the three groups of beads after the first round of coupling is shown at (a) of FIG. 15. The three groups of beads are then pooled together to randomize the beads. The beads are then again split into a number of subgroups. Another round of coupling then takes place wherein a second subunit is bonded to the first subunit already present on each bead (b). The process is then repeated (level (c) and beyond) (theoretically ad infinitum) until the desired chain length is attained.

The split and pool process is highly flexible and has the capability of generating literally millions of different compounds which, in certain applications, can be assayed for activity while still attached to the inert substrate. This makes it very easy to run in vitro assays on whole sub-libraries of compounds, while the sub-library is still attached to the beads. Then, as a matter of expediency, those sub-libraries which exhibit remarkable MMP-inhibitory activity as compared to the others would be deconvoluted first and the individual compounds tested.

One deconvolution strategy is depicted at levels (d), (e), and (f) of FIG. 14. Here, a selected pool of beads from the final round of coupling, in this instance, those beads having a terminal "H" subunit are screened for MMP-inhibitory activity. The best beads are then re-synthesized so that every bead has a terminal "H" group, and a known group next to "H," such as "D," "E," or "F" as shown in level (d). At level (e) of FIG. 14, one of the three resultant pools of beads is again selected and screened for MMP-inhibitory activity. The process is then repeated to yield a pool of 3-mers of known composition (level (f) of FIG. 14). These compounds are then screened for MMP activity to determine which individual compounds are the most potent MMP inhibitors.

A critical aspect of the split and pool methodology is that each reaction be driven to completion prior to initiating a subsequent round of coupling. So long as each coupling reaction is driven to completion, each substrate bead will only display a single compound. Because the rate of reaction will differ from bead to bead as the library construction progresses, the beads can be monitored using conventional dyes to ensure that coupling is completed prior to initiating another round of synthesis. The presence of only a single compound per bead comes about because each individual bead encounters only one incoming residue at each coupling cycle. So long as the coupling cycle is driven to completion, all available coupling sites on each bead will be reacted during each cycle and therefore only one type of peptoid will be displayed on each bead.

The resulting combinatorial library is comprised of a plurality of inert substrates, each having covalently linked thereto a different peptoid compound according to the present invention. The peptoids can be screened for MMP-inhibitory activity while still attached to the inert support, if so desired and feasible for the assay being utilized. Beads which display the desired activity are then isolated and the polypeptide contained thereon characterized via conventional peptide chemistry, such as the Edman degradation or via the deconvolution scheme described immediately above. Where a solution-phase assay is to be used to screen the library, the peptoids are cleaved from the solid substrate and tested in solution. The compounds need not be screened individually, but can be subjected to a gross "first pass" screen by evaluating small libraries or sub-libraries of compounds.

As applied in the present invention, one or more of the subunits coupled to the inert substrate are selected from the peptoid residues described herein. All of the compounds share a urea skeleton, which can then be modified in any desired fashion to yield the subject compounds In this manner, large libraries of peptoid MMP inhibitors can be assembled and screened for biological activity quickly and easily.

An alternative approach to generating combinatorial libraries uses parallel synthesis. In this approach, a known set of first subunits is covalently linked to a known location on a inert substrate, one subunit type to each location. The substrate may be a series of spots on a suitable divisible substrate such as filter paper or cotton. A substrate commonly used is an array of pins, each pin being manufactured from a suitable resin, described above.

After the initial round of coupling, each pin of the array bears a first subunit covalently linked thereto. The array is then reacted with a known set of second subunits, generally different from the first, followed by reactions with a third set of subunits, and so on (using the chemistry described hereinabove). During each reiteration, each individual pin (or location) is coupled with a incoming subunit selected from a distinct set of subunits, with the order of the subunits being recorded at each step. The final result is an array of peptoid compounds, with a different compound bonded to each solid substrate. Because the ordering of the subunits is recorded, the identity of the primary sequence of the peptoid at any given location on the substrate (i.e., any given pin) is known. As in the split and pool method, each coupling reaction must be driven to completion in order to ensure that each location on the substrate contains only a single type of peptoid.

Screening Compounds for Metalloproteinase Inhibitory Activity

The ability of candidate compounds to inhibit MMP's, in particular Type IV collagenases such as MMP-2 and MMP-9, may be evaluated using standard MMP assays. Typically such assays measure the ability of MMP's to catalyze the breakdown of gelatin or collagen. Appropriate assay conditions are described in U.S. Pat. No. 4,743,587, incorporated herein by reference; and in Cawston et al. (1979) *Anal. Biochem.* 94:340–345; and Weingarten et al. (1984) *Biochem. Biophys. Res. Commun.* 134:1184–1187. However, any standard assay for measuring MMP activity may be used.

Generally, to evaluate the therapeutic activity of the subject compounds, the relative ability of the compounds to inhibit a collagenase, preferably a type IV collagenase, and most preferably MMP-2 or MMP-9, is determined. A mounting body of evidence indicates that these two MMP's play an essential role in the degradation of basement membranes. This degradation is believed to be related to the ability of certain cells (e.g., tumor cells) to invade basement membranes which is, in turn, believed to play an integral role in metastasis, vascular leakage syndrome, septic shock, and other ailments.

Biochemical assays to determine collagenase inhibition include the following methods:

i) measuring in vitro the ability of a candidate compound to inhibit biochemical degradation of gelatin by a collagenase, e.g., MMP-2 or MMP-9;

ii) measuring in vitro the ability of a candidate compound to inhibit biochemical degradation of collagen IV by a Type IV collagenase; and iii) measuring in vitro the ability of a candidate compound to inhibit gelatinase activity of cell supernatants (containing various MMP's) run on and SDS-PAGE gel containing gelatin. This process is generally referred to as a zymogram.

Compounds which exhibit collagenase inhibitory activity in any of the above assays should possess potential utility for treating of septic shock, vascular leakage syndrome, or any other condition which is mediated, in whole or in part, by MMP's.

The MMP inhibitory activity of the subject compounds may also be determined on the basis of an in vitro cellular attachment assay. These types of assays measure the ability of certain cell types to attach to and/or to degrade basement membranes. These in vitro assays include the following methods:

i) determining whether the candidate compound inhibits attachment to basement membrane proteins;

ii) determining, in a modified Boyden chamber assay, whether the candidate compound inhibits directed motility of cells (e.g., tumor cells) to a chemoattractant; and iii) determining in the assay of(ii) whether the test compound inhibits in vitro invasion of isolated basement membrane proteins.

The preferred assay method to measure MMP inhibitory activity is a colorimetric assay which can be monitored spectrophotometrically. Specifically, the ability of the subject matrix metalloproteinase inhibitors to suppress MMP-2 or MMP-9 activity is assessed using a colorimetric 96-well thiopeptolide collagenase assay as described by Xia et al. (Xia T, Akers K, Eisen A Z and Seltzer J L. (1996) Biochim et Biophy Acta. 1293:259). This protocol entails the cleavage of a thiopeptolide substrate AcProLeuGly-S-LeuGlyOC$_2$H$_5$ (Bachem Bioscience, Cat # H7145) by MMP-2 or MMP-9, giving a free sulfhydryl group. The free —SH then reacts with DTNB (Ellman's reagent, 5,5'-dithiobis(2-nitrobenzoic acid)) giving a colored molecule whose formation can be examined spectrophotometrically at 405 nm.

The thiopeptolide substrate (5 μL/well, 5 mM in DMF), DTNB (15 μL/well, 10 mM in 50 mM HEPES, 10 mM CaCl2, pH 6.92), and matrix metalloproteinase inhibitors or DMSO (total volume equal to 5 μL/well) are mixed in a 96-well plate (Falcon). A single row of wells is used for each matrix metalloproteinase inhibitor and various inhibitor concentrations are used to control for row to row variation in collagenase activity. The reaction is then initiated by pipeting 130 μL of a solution of collagenase buffer (126 μL/well, 50 mM HEPES, 10 mM CaCl$_2$, pH 6.92) and activated MMP-2 or MMP-9 (4 μL/well, 0.05 M borate, pH 7.46, 5 mM CaCl$_2$, 20% glycerol, 0.0005% Brij-35) into a row of wells using a 12-channel multipipeter. The change in absorbance from 0–20 minutes is then monitored at 405 nm using an ELX 800 automated microplate reader (Bio-Tek Instruments, Inc., Winooski, Vt.). The change in absorbance is calculated and graphed.

For illustrations of this assay method, see the Examples hereinbelow.

Utility

The compounds of Formula I and II, including the pharmaceutically-acceptable salts and isomeric forms thereof, are useful to inhibit the activity of MMP's, especially MMP-2 and MMP-9. Consequently, these compounds and pharmaceutical compositions containing the compounds are useful to prevent and to treat pathophysiological conditions mediated in whole or in part, by the activity of MMP's, including septic and toxic shock, SIRS, and invasive and metastatic cancer.

Pharmaceutical Compositions

Another aspect of the invention provides pharmaceutical compositions, for medical use, comprising an active compound, i.e., a Formula I or II compound or a pharmaceutically-acceptable salt thereof, in combination with an acceptable carrier therefor and optionally with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal or parenteral (including subcutaneous, intramuscular and intravenous) administration.

The formulations may conveniently be presented in unit dosage form and may be prepared by any of the methods well known in the art of pharmacy. The term "unit dosage" or "unit dose" is denoted to mean a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound of Formula I or II which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

Compositions suitable for rectal administration, comprise a suppository, preferably bullet-shaped, containing the active ingredient and pharmaceutically-acceptable vehicles therefore such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefore such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the subject compounds are preferably utilized at concentrations of from about 5.0–10% by weight. Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of compounds of Formula I or II are preferably utilized at concentrations of from about 0.1% to 5.0% by weight applied to a dressing.

Compositions suitable for administration by inhalation include formulations wherein the active ingredient is a solid or liquid admixed in a micronized powder having a particle size in the range of about 5 microns or less to about 500 microns or liquid formulations in a suitable diluent. These formulations are designed for rapid inhalation through the oral passage from a conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of compound of Formula I or II required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose is in the range of about 0.1 to about 500 mg/kg body weight per day, preferably in the range of about 5 to about 350 mg/kg per day, calculated as the non-salt form of Formula I or II. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

In general, the pharmaceutical compositions of this invention contain from about 0.5 mg to about 1.5 g active ingredient per unit dose and, preferably, from about 7.5 to about 1000 mg per per unit dose. If discrete multiple doses are indicated, treatment might typically be 100 mg of a compound of Formula I or II given from two to four times per day.

The MMP inhibitors according to the present invention may be administered prophylactically, chronically, or acutely. For example, such compounds may be administered prophylactically to patients exhibiting infections in order to prevent the onset of vascular leakage syndrome or septic shock. The subject compounds may also be administered prophylactically to patients suffering a primary cancer to prevent the occurrence of metastatic cancers. In addition to the prevention of metastatic cancers, chronic administration of the subject compounds will typically be indicated in treating chronic collagenase-related disorders including inflammatory disorders such as arthritis. Acute administration of the subject compounds is indicated to treat, for example, the advanced stages of vascular leakage syndrome and septic shock.

EXAMPLES

The following Examples are included solely to provide a more complete understanding of the present invention. The Examples do not limit the scope of the invention disclosed and claimed herein in any fashion.

Example 1

Effect on F442 Fibroblast Viability

To be incorporated successfully into a pharmaceutical composition, a compound must assert its intended effect without having unacceptably high cytotoxicity within the window of therapeutically active drug concentration. This Example tests the in vitro effect of a series of the subject compounds, designated series 151.2, on the viability of cultured fibroblasts.

Toxicity of the compounds was determined by incubating several log doses of the compound and solvent controls for 6 to 24 hours in serum-free medium. The cell number was then determined by comparing the absorbance of crystal violet with controls, and cell death determined by trypan blue dye exclusion in conventional and well known fashion. The model cell line used was a murine fibroblast cell line designated F442A, which was generously provided by Dr. Howard Green of Harvard University.

The series 151.2 compounds are a sub-library of the subject compounds consisting of the following compounds:

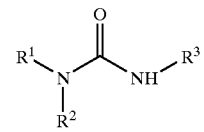

wherein $R^1$ is selected from

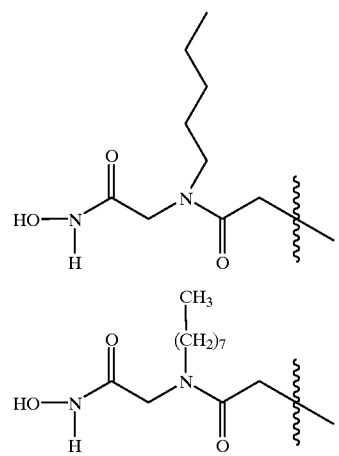
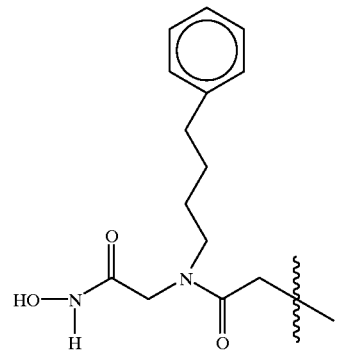
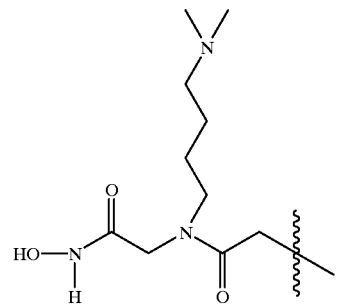

-continued

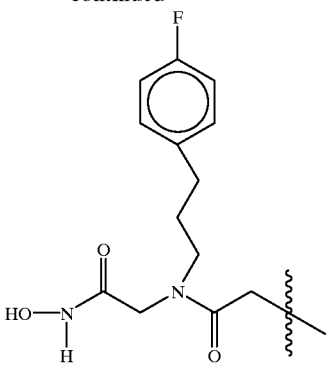

R² is selected from:

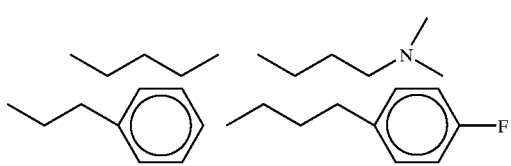

and R³ is:

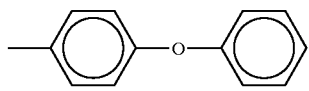

The compounds of series 151.2 were fabricated in combinatorial fashion using the split and pool methodology described herein. The compounds were cleaved from the beads into a single solution and tested in this combined fashion. The fibroblasts were cultured and exposed to solutions of series 151.2 compounds at concentrations of 0 (control), 1, 10, and 100 μM. The results are depicted graphically in FIG. 1. As can be seen from the figure, even at concentrations as high as 100 μM, the series 151.2 compounds had a negligible effect on the growth of the fibroblasts. This Example demonstrates the low cytotoxicity of the subject compounds.

Example 2

Effect on F442 Fibroblast Viability

In this Example, cultured fibroblasts are placed into the upper chamber of a two-chambered plate. The two chambers are separated by a perforated barrier which is just large enough for the fibroblast to pass through (if sufficiently motivated). A chemoattractant is placed into the lower chamber to entice the fibroblasts to migrate from the upper chamber into the lower. In this case, epidermal growth factor (EGF) plus fibronectin was used as the chemoattractant.

Figure 2:
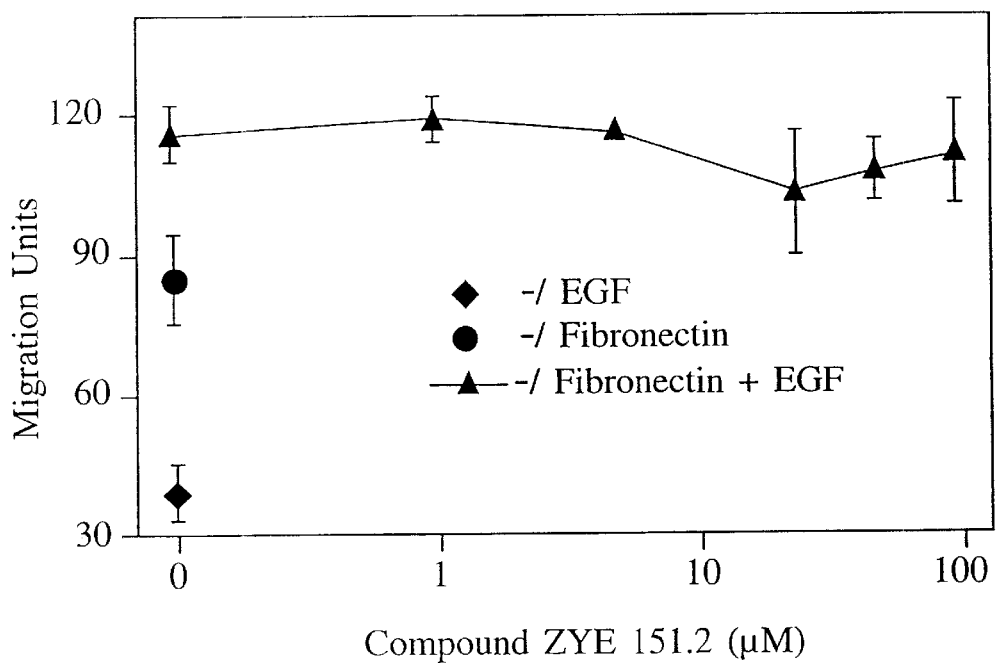
FIG. 2 is a graph depicting the in vitro effect of the same subset of compounds as depicted in FIG. 1 on F442A fibroblast migration. See Example 2
Figure 2:
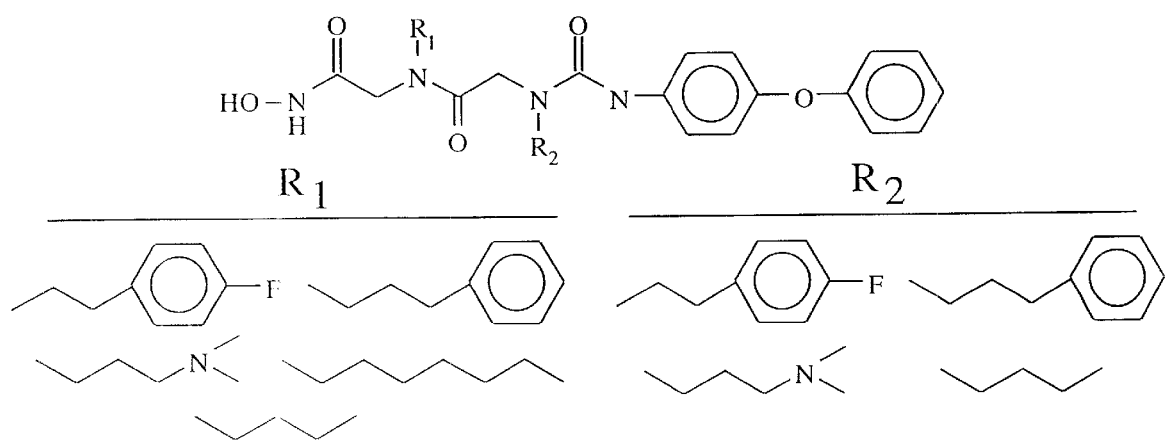

Cultured F442 fibroblasts were placed into the upper chambers of a series of wells in the presence of 0 (control), 1, 10, and 100 μM of series 151.2 compounds. Into the lower chambers was placed either EGF, fibronectin, or EGF and fibronectin. The results are depicted in FIG. 2. As shown in the figure, when migration was initiated by the presence of EGF and fibronectin in the lower chamber, the motility of the fibroblasts was not significantly altered by the presence of up to 100 μM of series 151.2 compounds. The Example shows that not only are the subject compounds of low toxicity, they also do not have any adverse effect upon the mobility of fibroblasts. Fibroblast mobility is key to the repair of injured basement membranes.

Example 3

In Vitro Invasion Assay

In this Example, the series 151.2 compounds were tested in an in vitro assay for their ability to inhibit tumor cell penetration of a reconstituted basement membrane known as as "MATRIGEL" (Collaborative Biomedical Products Inc., Bedford, Mass.) (see Kleinman et al. (1982) Biochem. 24:6188–6193).

An 8 μm pore filter coated with "MATRIGEL" separates a series of lower compartments containing a chemoattractant and a corresponding series of upper compartments containing metastatic and non-metastatic cells and a compound to be tested. The metastatic cells are able to degrade the "MATRIGEL" barrier and, over a period of time, migrate through the pores of the filter whereas non-metastatic cells remain on the upper surface. The cells that pass to the underside of the filter are counted under a microscope to determine the extent to which they are able to pass from the upper compartment into the lower compartment. The ability of tumor cells to penetrate "MATRIGEL" has been shown to depend upon the degradation of Type IV collagen in the "MATRIGEL" by Type IV collagenases (Reich et al. (1988) Cancer Res. 48:3307–3312). Variations of this assay have been used: 1) to correlate the extent of in vitro invasion with metastatic potential in vivo (see Albini et al. (1987) Cancer Res. 47:3234–3245; Hendrix et al. (1987) Cancer Letters 38:127–247; and Repesh L. A. (1989) Invasion Metastasis 9:192–208); 2) to select for more highly invasive cells (Teranova et al. (1986) Proc. Nat. Acad. Sci. 83:464–465; Tullberg et al. (1989) Invasion Metastasis 9:13–26; and Sefer et al. (1990) Biotechniques 9:324–331); and 3) to test compounds for inhibition of degradation activity (Nakajima et al. (1989) Cancer Res. 49:1698–1756).

This method has been refined to increase the number of assays which may be performed and analyzed per day. In particular, such improvement comprises using disposable "Transwell" units described by Repesh et al. (1989) Invasion Metastasis 9:192–208. These units comprise an 8 μm pore filter attached to an insert that fits into a 24-well culture plate. The "MATRIGEL" concentration in the unit is titrated from 0% inhibition to 100% inhibition of motility of each invasive cell line used in the assay and for each batch of "MATRIGEL." The "MATRIGEL" concentration which yields 50% or greater inhibition of motility in a 6 hour assay (usually from 15 to 50 μg of protein per filter) is chosen for determination of invasion. Motility of the cells through the 8 μm filters is not by passive diffusion since the pore size is smaller than the cells, and is determined in the same chamber in the absence of "MATRIGEL". Motility is stimulated two-fold by the presence of fibroblast-conditioned medium (3T3 cells) as a chemoattractant. The cell line used in this example was HiMel, a highly malignant, highly invasive human melanoma, generously provided by Dr. Joseph Seltzer of Washington University in St. Louis.

Compounds to be tested were dissolved in DMSO and were added in serial dilutions of 0 (control) 1, and 10 μM. For inhibition studies, 5×10⁵ cells were plated in 200 μl of DMEM, 0.1% BSA, and the test compound (or appropriate solvent control) into the upper compartment of the plate. To the bottom compartment of the plate, in contact with the underside of the "Transwell" filter unit, is added 800 μl of 3T3-conditioned medium containing DMEM and 2%

"NuSerum" (Collaborative Research Inc.). For inhibition of invasion, the filters are pre-coated with "MATRIGEL" at the appropriate concentration. The assays were run at 37° C. for 6 hours. At the end of the assay the entire filter was stained and fixed in 0.5% crystal violet in 20% methanol for 15 min. The filters were then rinsed in water and the non-invasive cells remaining on the upper surface of the filters were wiped off with a cotton swab. Invasive cells found on the under side of the filter were measured by solubilizing the stain in 10% acetic acid 20% methanol and reading the absorbance at 595 nm.

Figure 3:
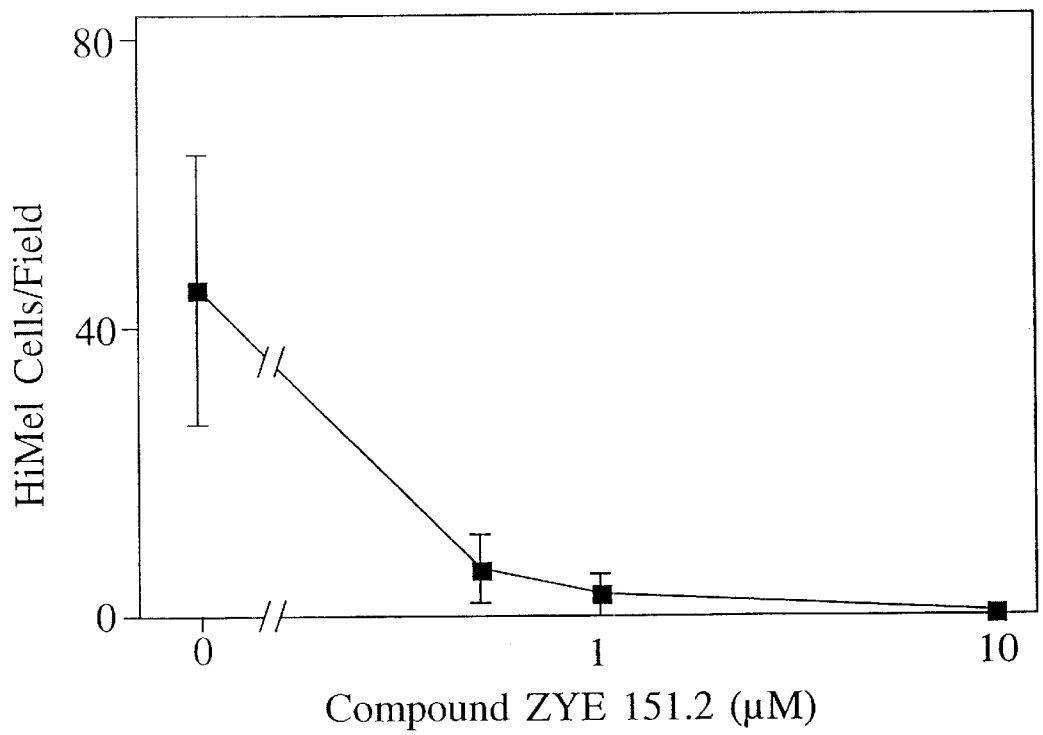
FIG. 3 is a graph depicting the in vitro inhibitory effect of the same subset of compounds as depicted in FIG. 1 on the invasion of HiMel cells (a highly malignant, human cancer cell line) into "MATRIGEL" collagen. See Example 3
Figure 3:
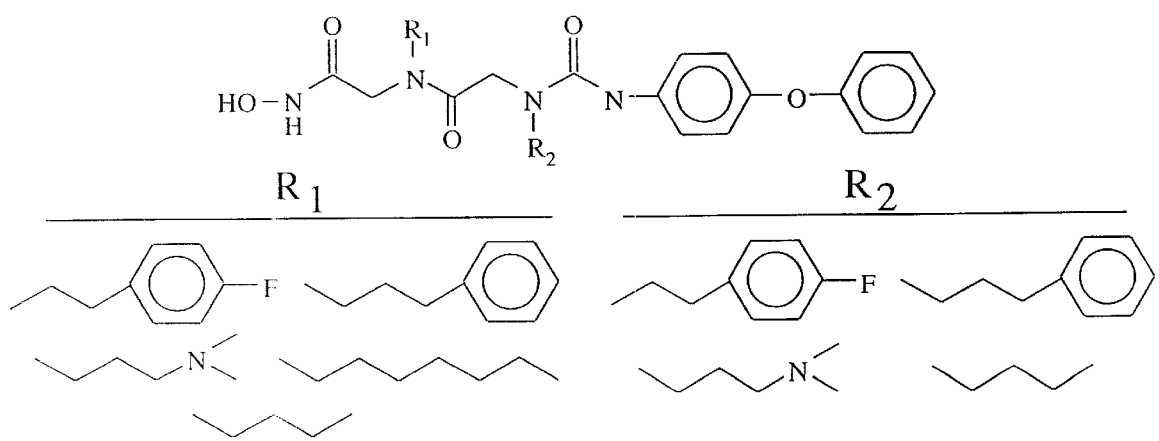

The results are shown in FIG. 3. At concentrations less than 1 μM, the series 151.2 compounds had a pronounced inhibitory effect on the ability of the HiMel cells to penetrate the "MATRIGEL." This Example illustrates the utility of the subject compounds to prevent invasive cancers from penetrating collagen membranes.

Example 4

Effects on MMP-2 Collagenase Activity

Here, the colorimetric assay described above was used to measure the inhibitory effect of the following compound on the collagenase activity of MMP-2:

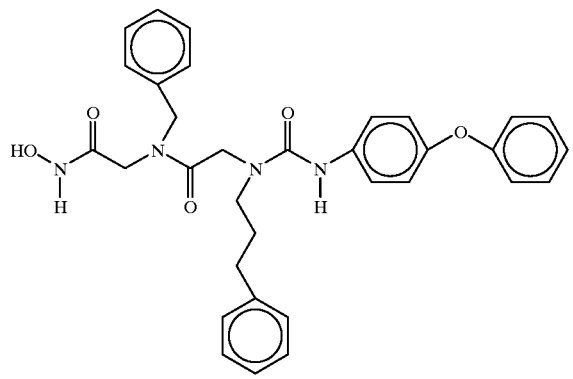

The thiopeptolide substrate AcProLeuGly-S-LeuGlyOC$_2$H$_5$ (5 μL/well, 5 mM in DMF), DTNB (15 μL/well, 10 mM in 50 mM HEPES, 10 mM CaCl2, pH 6.92), and matrix metalloproteinase inhibitors or DMSO (total volume equal to 5 μL/well) were mixed in a 96-well plate. A single row of wells was used for each concentration of the test compound and concentrations of 10, 20, and 40 μM of the test compound were used. The reaction was then initiated by pipeting 130 μL of a solution of collagenase buffer (126 μL/well, 50 mM HEPES, 10 mM CaCl$_2$, pH 6.92) and activated MMP-2 (4 μL/well, 0.05 M borate, pH 7.46, 5 mM CaCl$_2$, 20% glycerol, 0.0005% Brij-35) into a row of wells using a 12-channel multipipeter. The change in absorbance from 0–20 minutes was then monitored at 405 nm. The change in absorbance was calculated and graphed; the results are depicted in FIG. 4.

Figure 4:
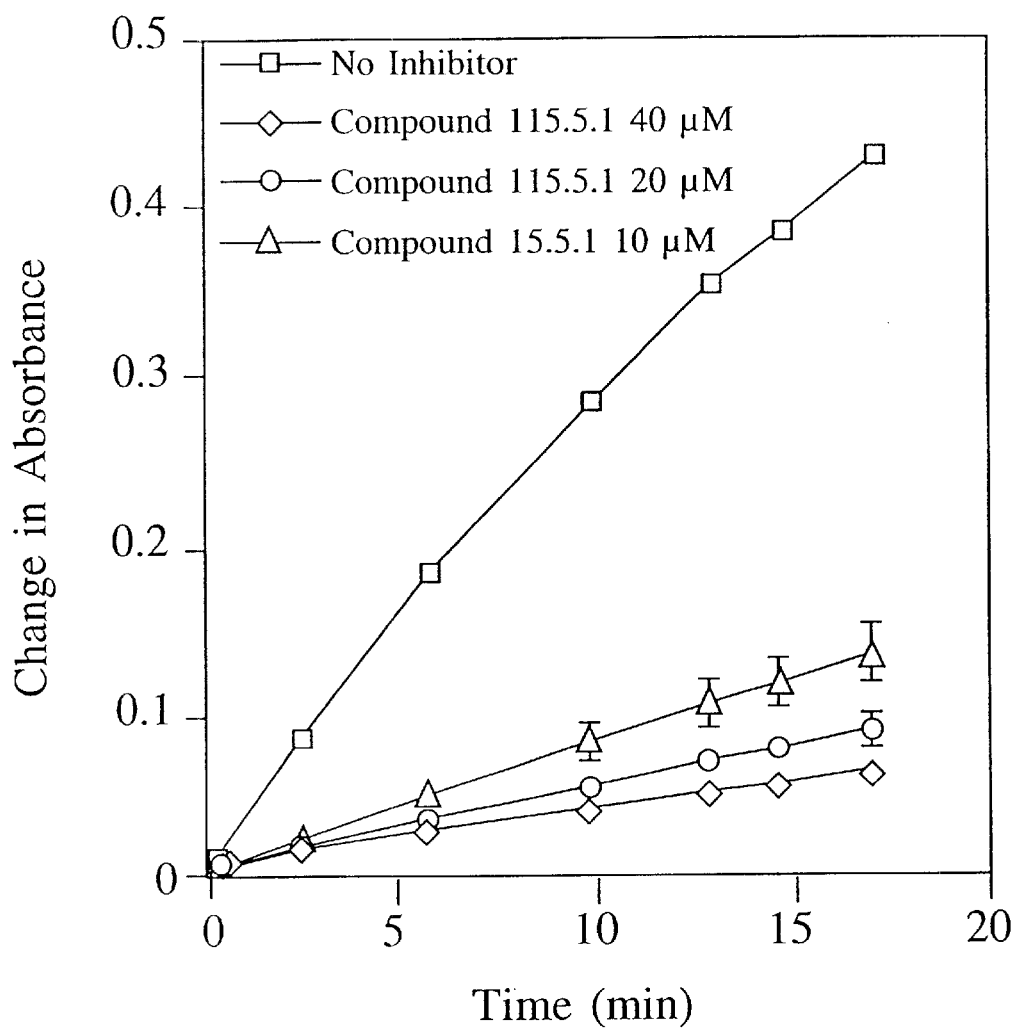
FIG. 4 is a graph depicting the in vitro MMP-2 inhibitory effect of various concentrations of a compound according to the present invention See Example 4.
Figure 4:
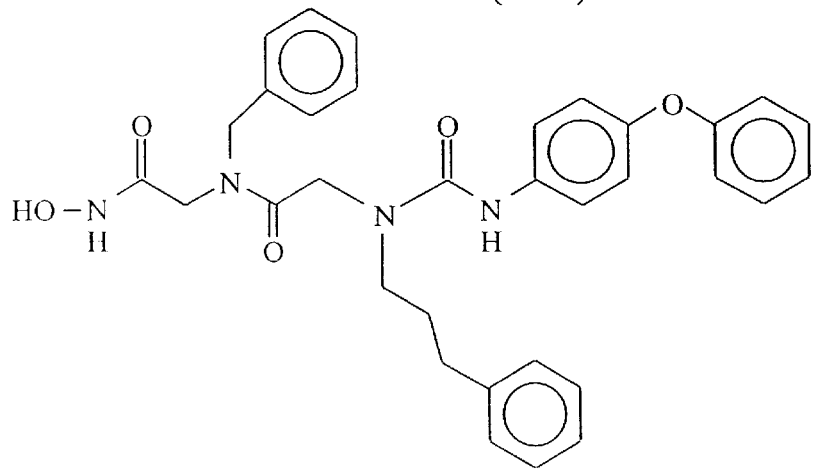

As is clearly shown in FIG. 4, the test compound inhibited MMP-2 collagenase activity in a dose-dependent manner. This Example demonstrates the utility of the subject compounds to inhibit MMP activity.

Example 5

Effect on F442 Fibroblast Viability

Figure 5:
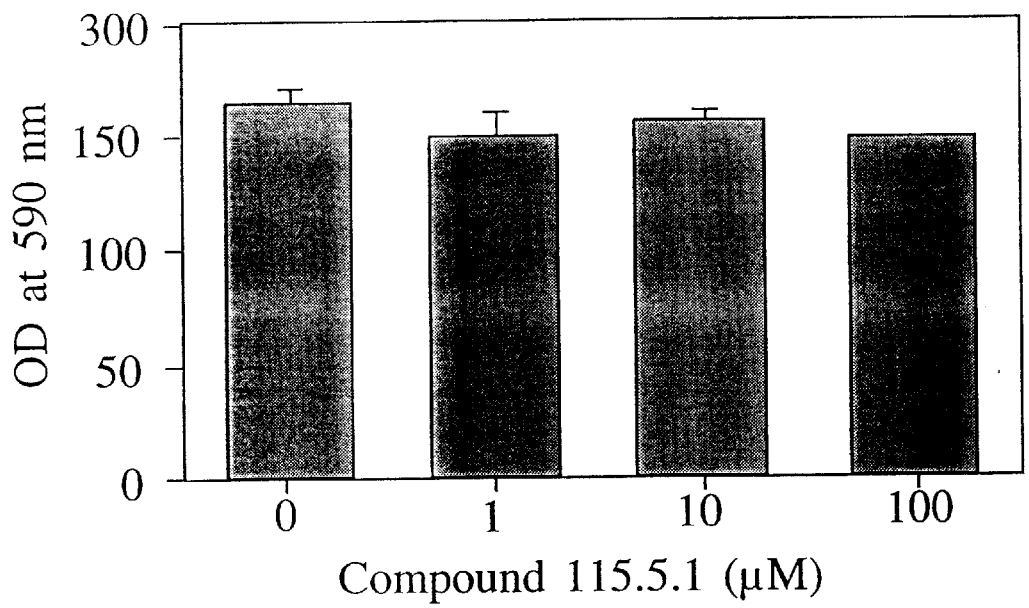
FIG. 5 is a graph depicting the in vitro effect of the compound of FIG. 4 on F442A fibroblast viability. See Example 5
Figure 5:
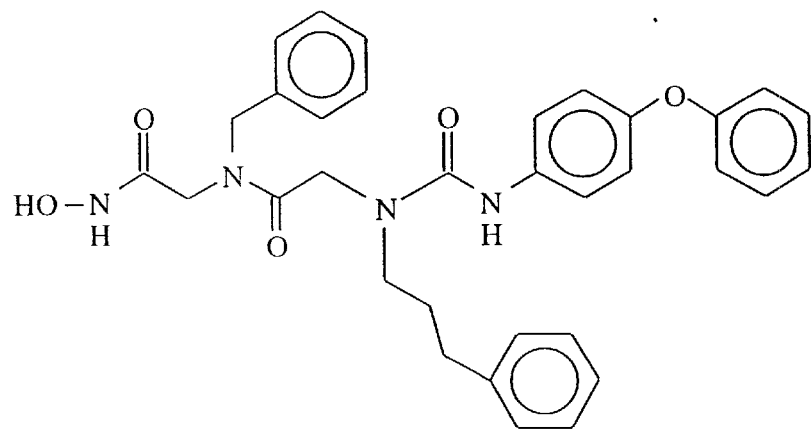

This Example was performed in the exact same fashion as Example 1, with the exception that the test compound used in Example 4 was evaluated for its effect on fibroblast viability. The results are shown in FIG. 5. The figure indicates that at concentrations up to 100 μM, this compound had no significant effect on the viability of fibroblasts.

Example 6

In Vitro Invasion Assay

Figure 6:
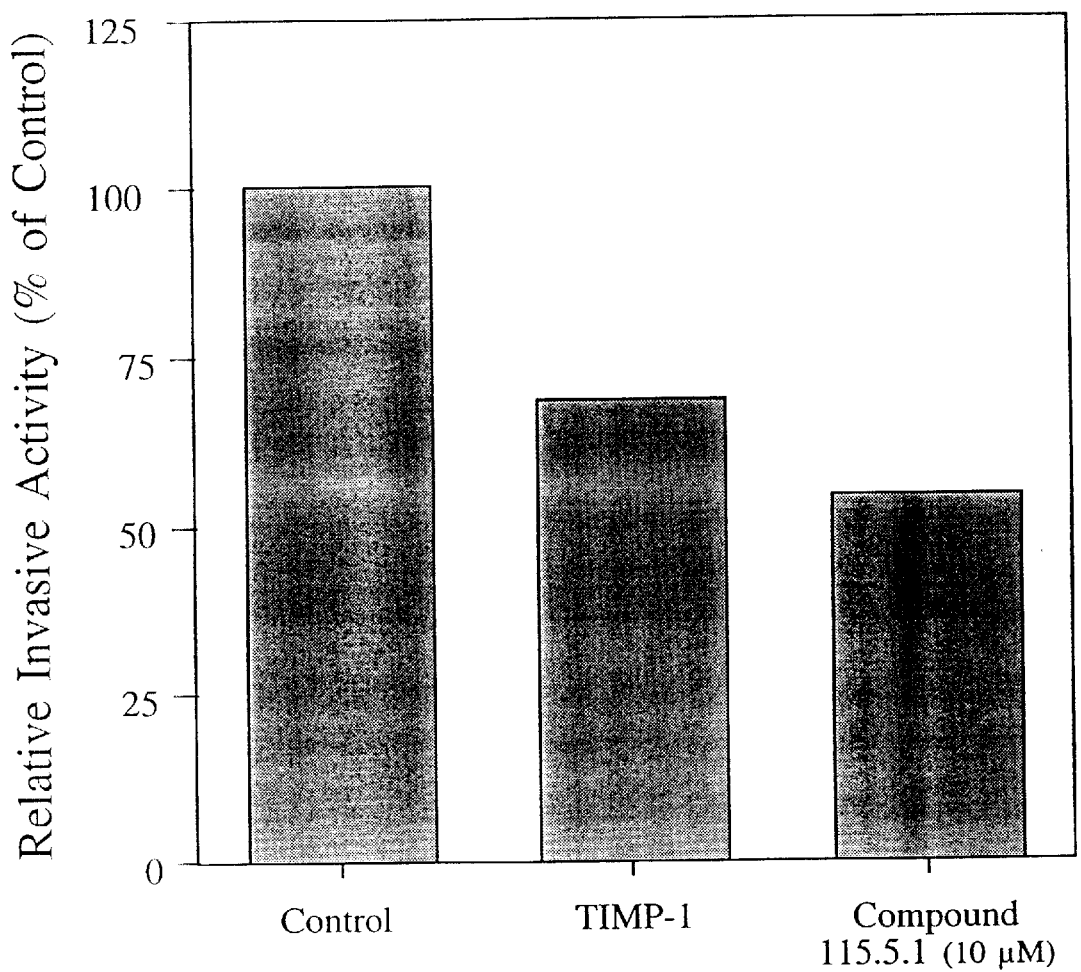
FIG. 6 is a graph depicting the in vitro inhibitory effect of compound of FIG. 4 on the invasion of HiMel cells into "MATRIGEL" collagen. See Example 6.
Figure 6:
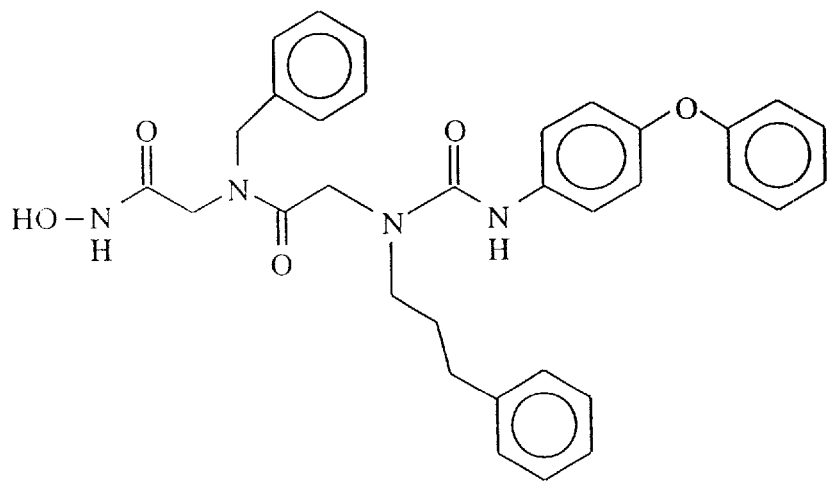

Here, the compound tested in Examples 4 and 5 was evaluated for its ability to inhibit the invasion of MATRIGEL by HiMel cells using the same assay described in Example 3. The results are depicted graphically in FIG. 6. Here, the figure clearly shows that the test compound exhibited approximately 50% inhibition of HiMel "MATRIGEL" invasion as compared to the control.

Example 7

Effects on MMP-2 Collagenase Activity

Here, the colorimetric assay described in Example 4 was used to evaluate the following compound for its MMP inhibitory activity:

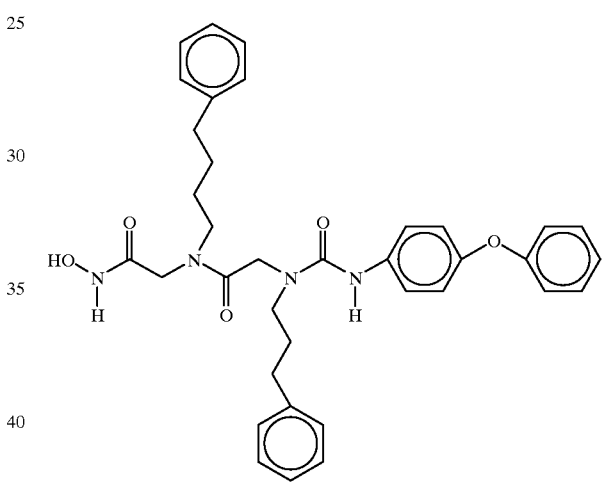

Figure 7:
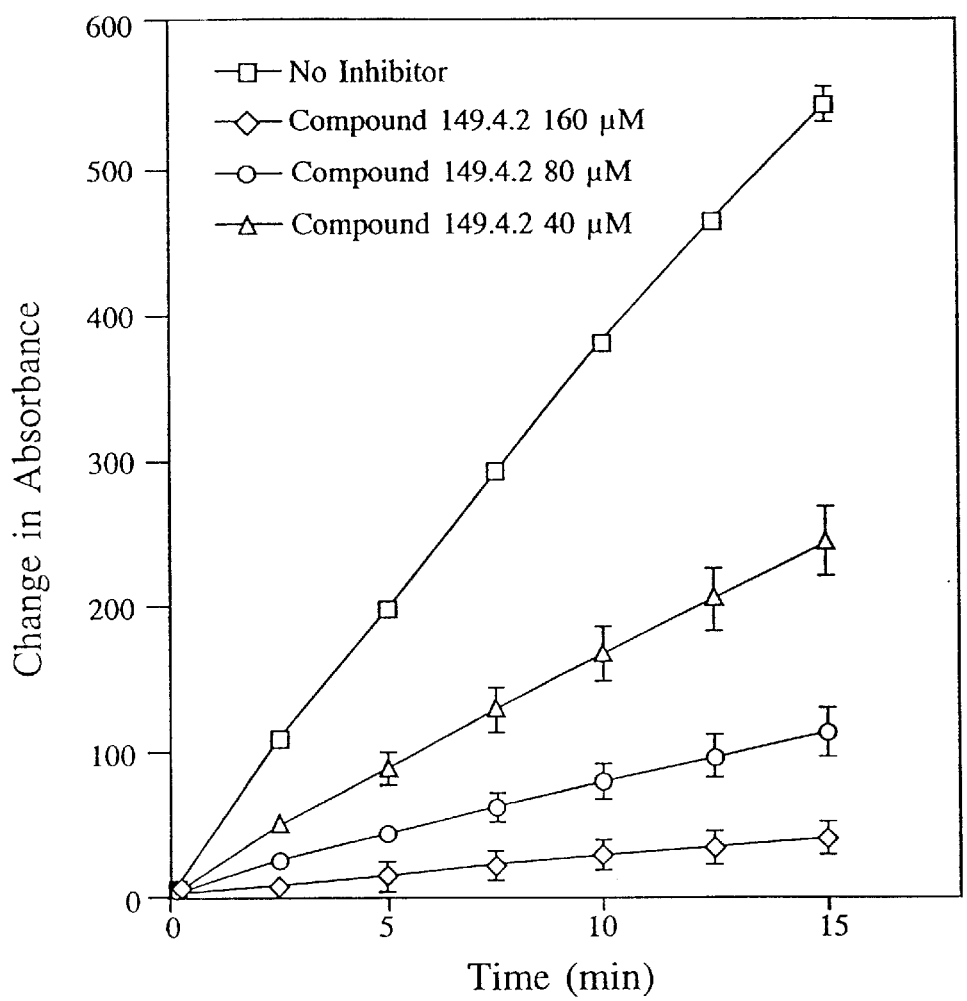
FIG. 7 is a graph depicting the in vitro MMP-2 inhibitory effect of various concentrations of another compound of the invention. See Example 7.
Figure 7:
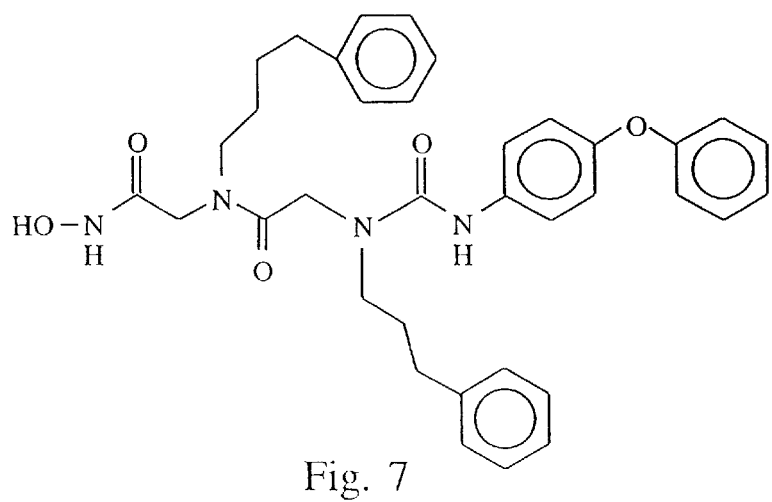

The results are shown in FIG. 7. In this Example, the test compound was evaluated at concentrations of 0 (control) 40, 80, and 160 μM. As can be seen from the figure, the test compound inhibits MMP-2 collagenase activity in a dose-dependent fashion.

Example 8

Effect on F442 Fibroblast Viability

Figure 8:
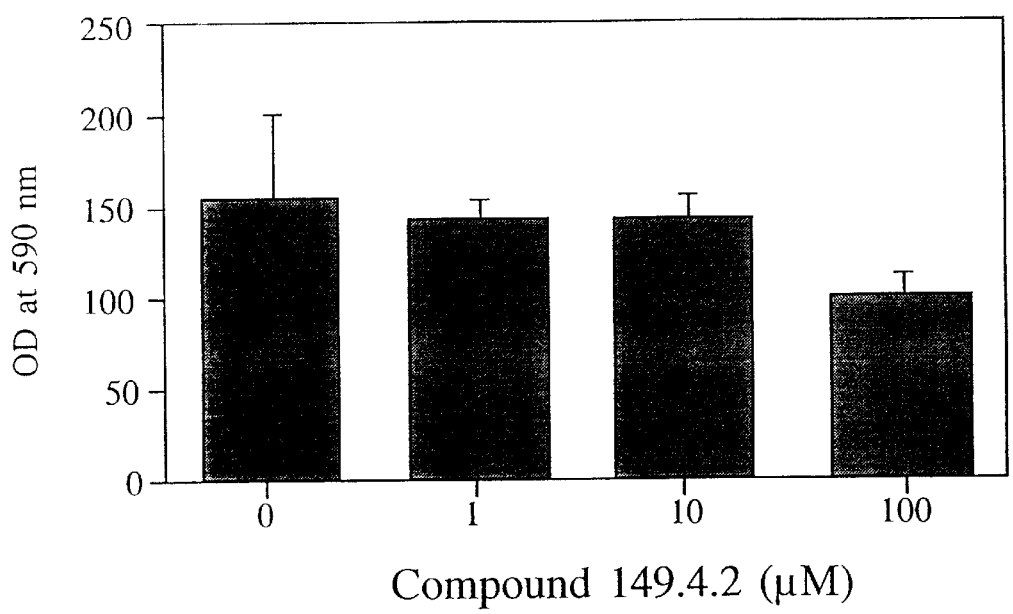
FIG. 8 is a graph depicting the in vitro effect of the compound of FIG. 7 on F442A fibroblast viability. See Example 8.
Figure 8:
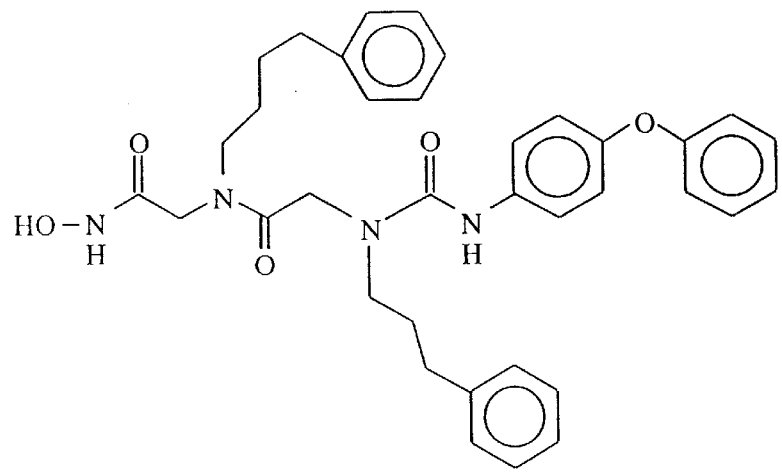

This Example was performed in the exact same fashion as Example 1, with the exception that the test compound used in Example 7 was evaluated for its effect on fibroblast viability. The results are shown in FIG. 8. The figure indicates that at concentrations up to 100 μM, this compound had no significant effect on the viability of fibroblasts.

Example 9

Effects on MMP-2 Collagenase Activity

Here, the colorimetric assay described in Example 4 was used to evaluate the following amine-terminated compound for its MMP inhibitory activity:

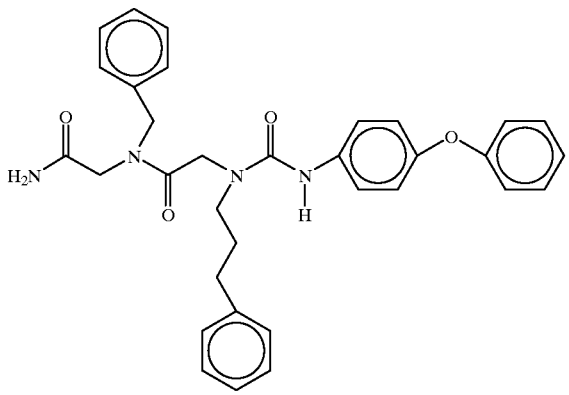

Figure 9:
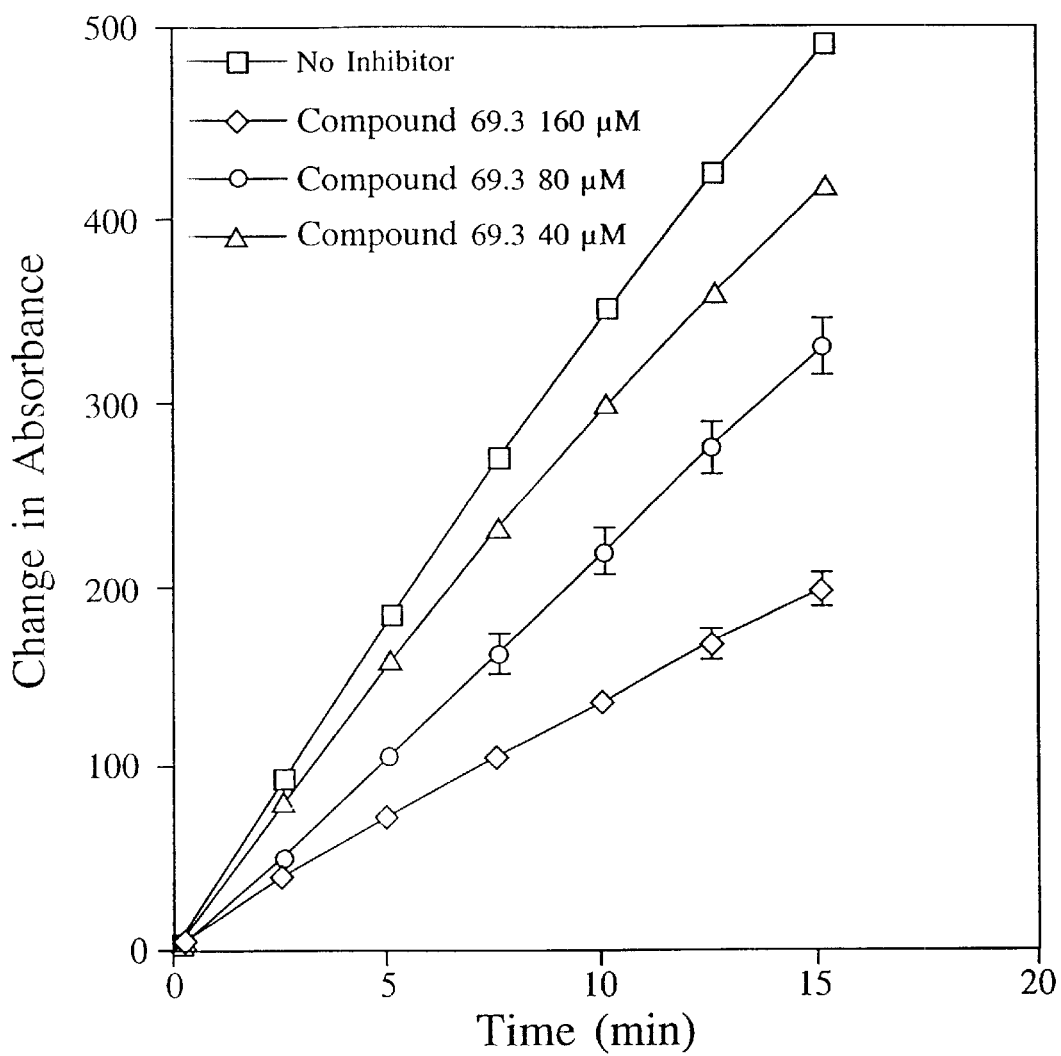
FIG. 9 is a graph depicting the in vitro MMP-2 inhibitory effect of various concentrations of yet another compound of the invention. See Example 9.
Figure 9:
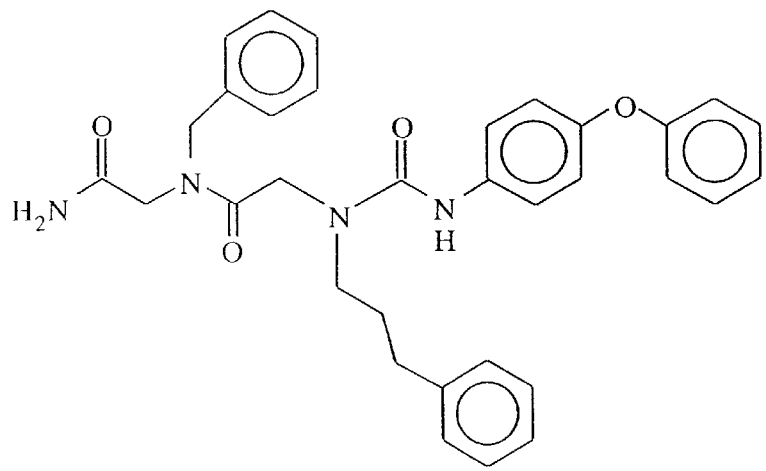

The results are shown in FIG. 9. In this Example, the test compound was evaluated at concentrations of 0 (control) 40, 80, and 160 μM. As can be seen from the figure, the test compound inhibits MMP-2 collagenase activity in a dose-dependent fashion.

Example 10

Effects on MMP-2 Collagenase Activity

Here, the colorimetric assay described in Example 4 was used to evaluate the following compound for its MMP inhibitory activity:

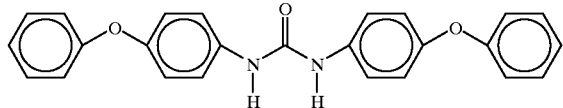

Figure 10:
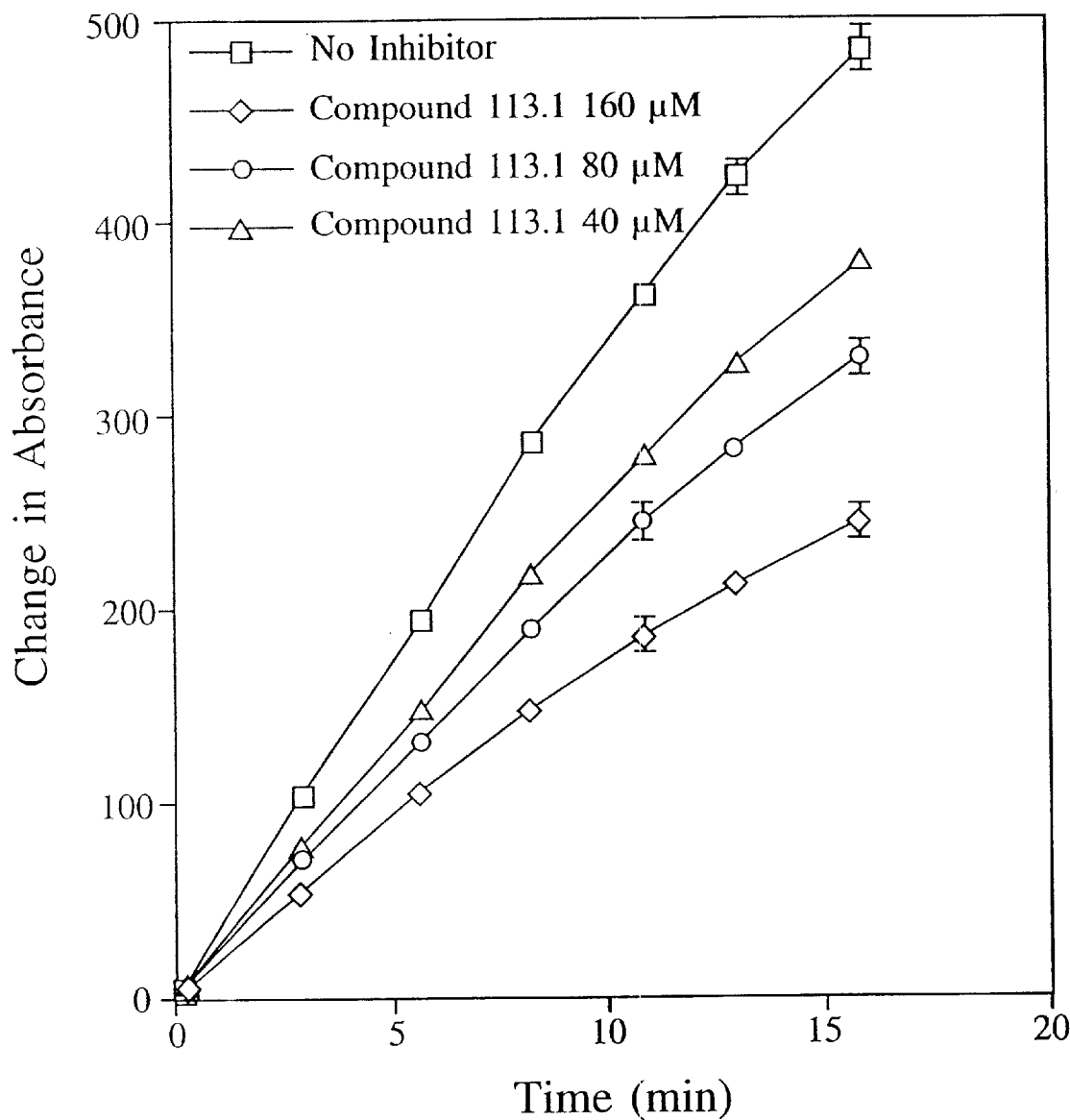
FIG. 10 is a graph depicting the in vitro MMP-2 inhibitory effect of various concentrations of still another compound according to the invention. See Example 10.
Figure 10:
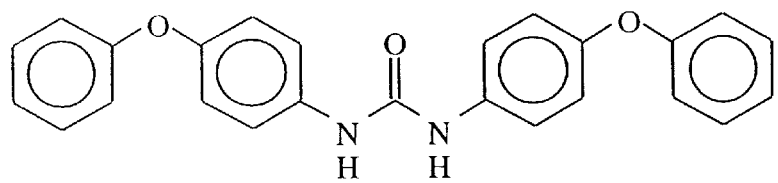

The results are shown in FIG. 10. In this Example, the test compound was evaluated at concentrations of 0 (control) 40, 80, and 160 μM. As can be seen from the figure, the test compound inhibits MMP-2 collagenase activity in a dose-dependent fashion.

Example 11

Effects on MMP-2 Collagenase Activity

Here, the colorimetric assay described in Example 4 was used to evaluate the following compound for its MMP inhibitory activity:

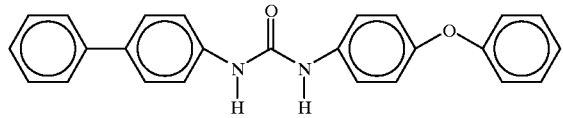

Figure 11:
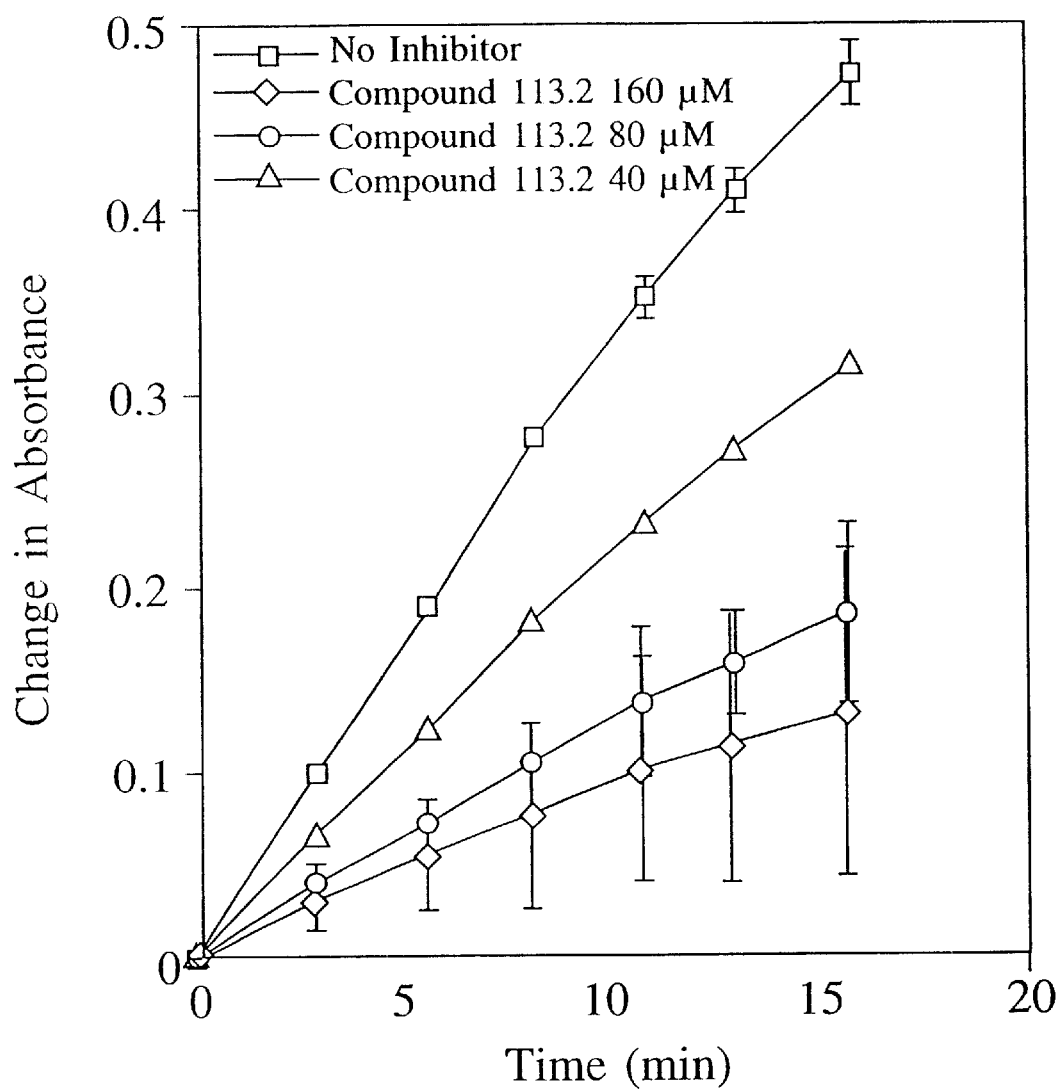
FIG. 11 is a graph depicting the in vitro MMP-2 inhibitory effect of various concentrations of yet another compound of the invention. See Example 11.
Figure 11:
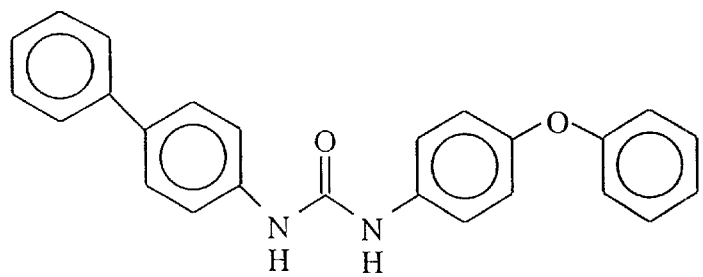

The results are shown in FIG. 11. In this Example, the test compound was evaluated at concentrations of 0 (control) 40, 80, and 160 μM. As can be seen from the figure, the test compound inhibits MMP-2 collagenase activity in a dose-dependent fashion.

Example 12

In Vitro Invasion Assay

Figure 12:
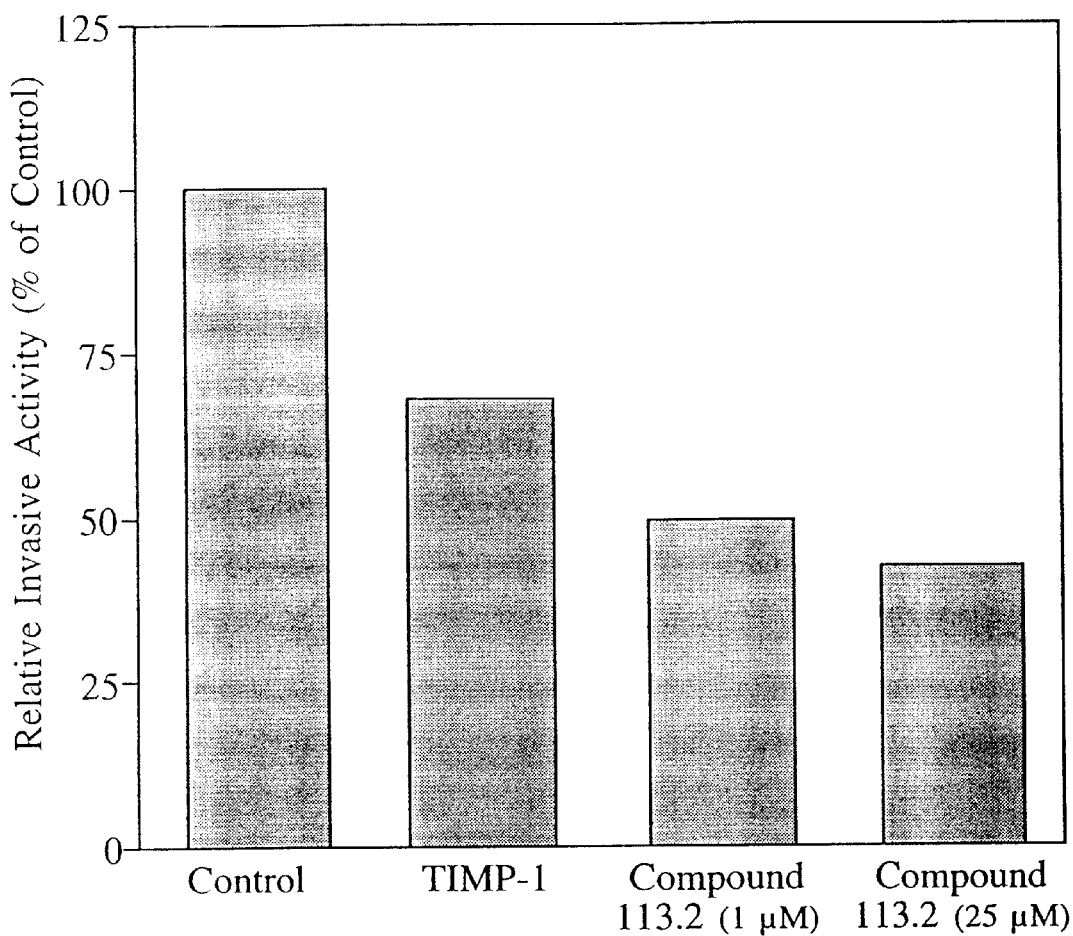
FIG. 12 is a graph depicting the in vitro inhibitory effect of the compound of FIG. 11 on the invasion of HiMel cells into "MATRIGEL" collagen. See Example 12.
Figure 12:
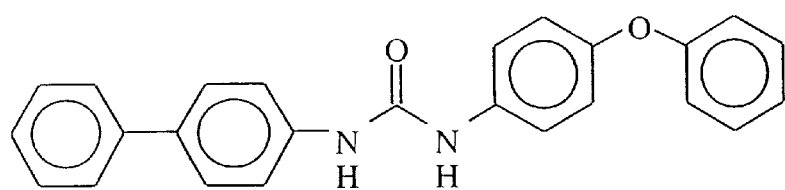
Figure 13:
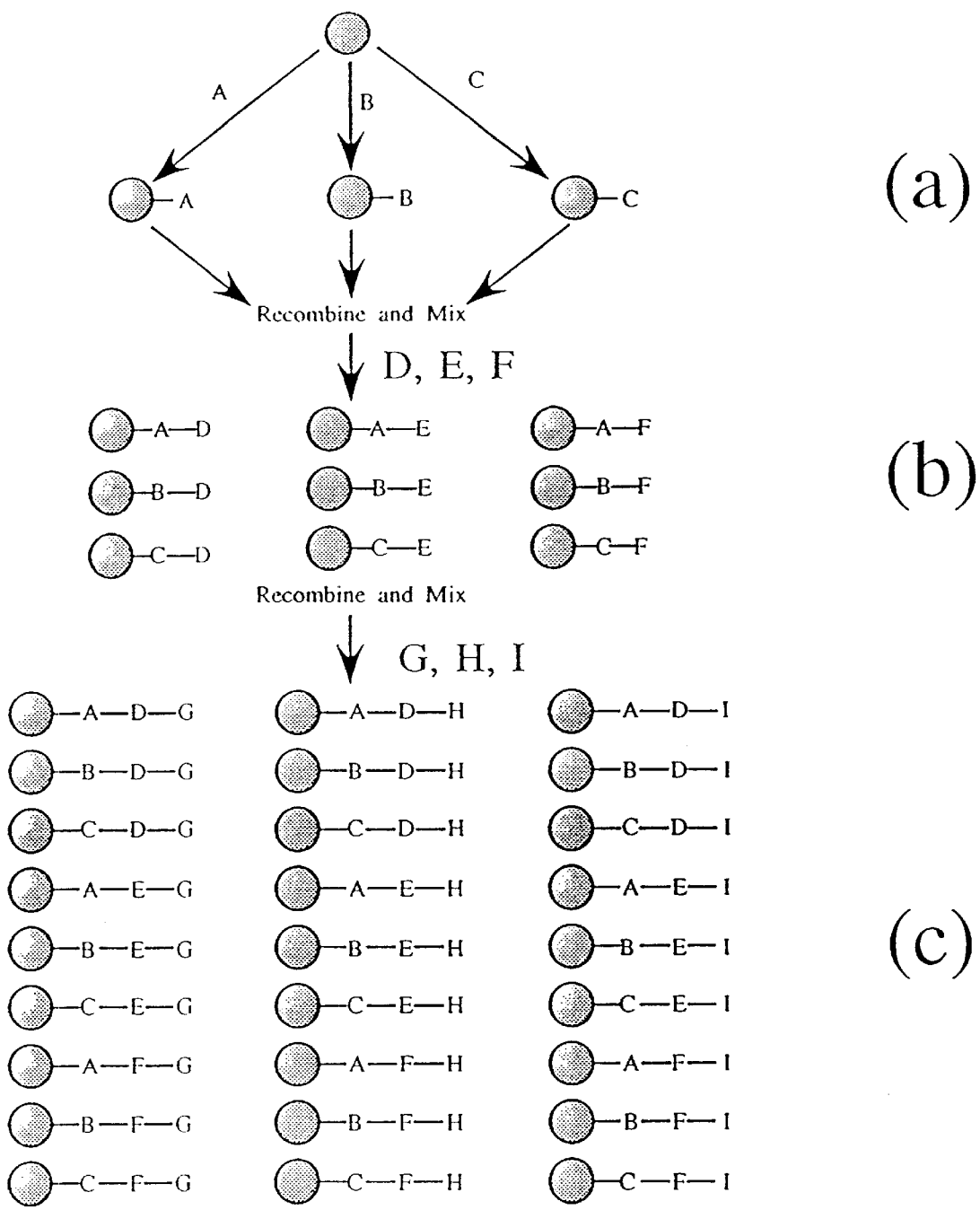
FIG. 13 is a schematic representation of the "split and pool" method of generating combinatorial libraries and a method to deconvolute the libraries.
Figure 13:
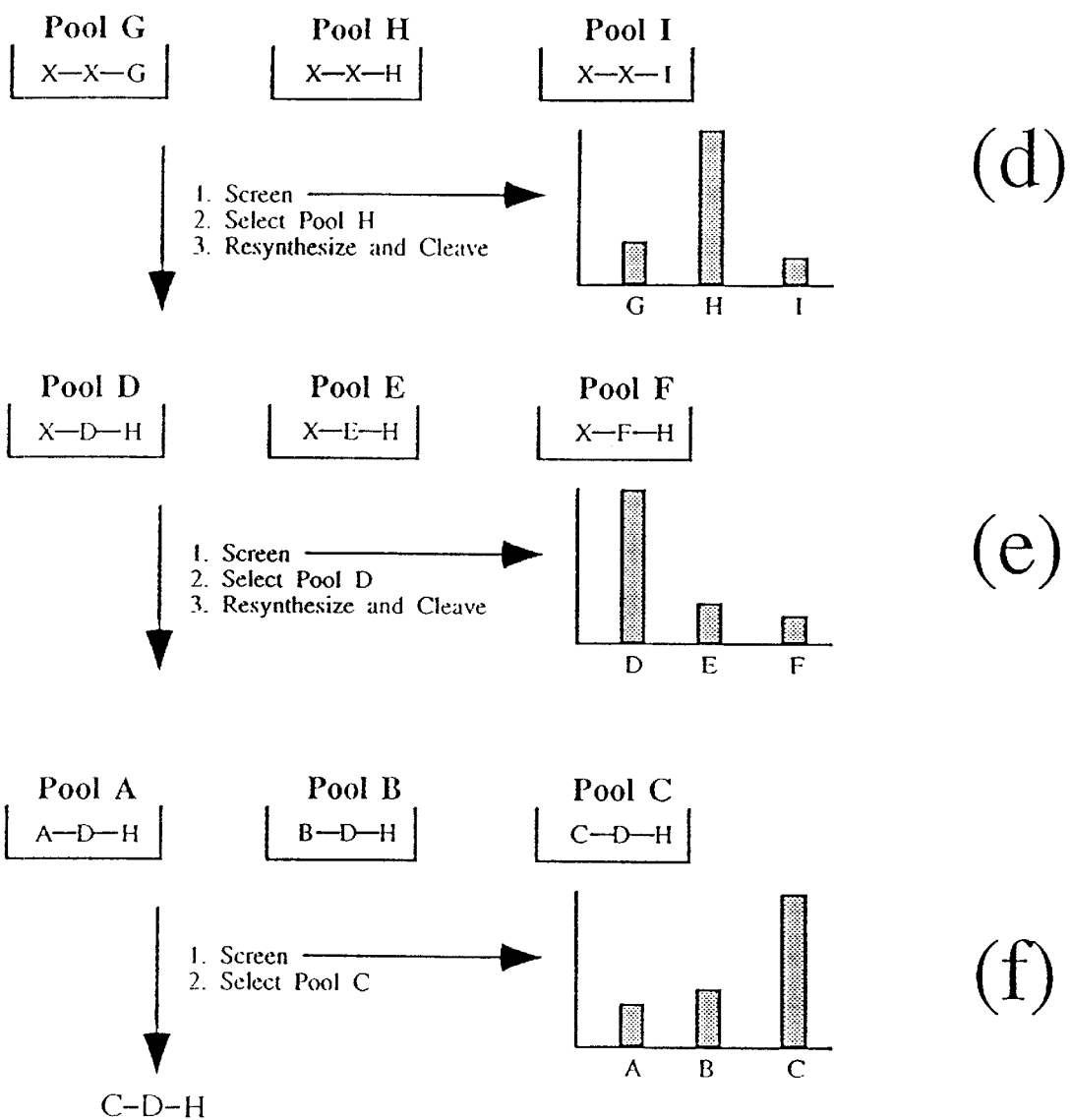

Here, the compound tested in Example 11 was evaluated for its ability to inhibit the invasion of MATRIGEL by HiMel cells using the same assay described in Example 3. The results are depicted graphically in FIG. 12. Here, the figure clearly shows that the test compound exhibited approximately 50% inhibition of HiMel "MATRIGEL" invasion as compared to the control.

Example 13

Effects on MMP-2 Collagenase Activity

Here, the colorimetric assay described in Example 4 was used to evaluate the following series of compounds for their MMP inhibitory activity. The results are reported as $IC_{50}$ concentration in μM for various sub-libraries of the series.

The compounds consisted of the following structures:

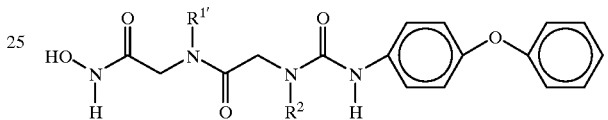

wherein $R^1$ was selected from:

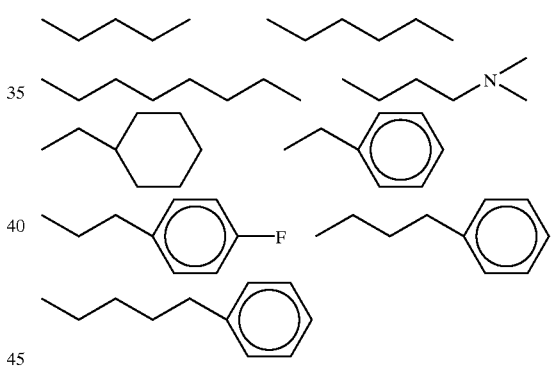

and when $R^2$ was:

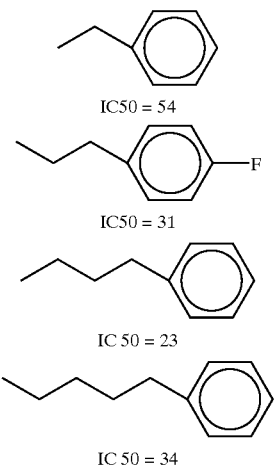

IC50 = 54

IC50 = 31

IC 50 = 23

IC 50 = 34

-continued

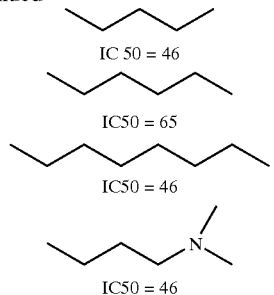

IC 50 = 46

IC50 = 65

IC50 = 46

IC50 = 46

The invention is not limited to the particular reagents, protocols, etc. described hereinabove, but includes all modified and equivalent forms thereof which are within the scope of the following claims.

What is claimed is:

1. A method of treating systemic inflammatory response syndrome in mammals comprising administering to the mammal an effective MMP-inhibitory amount of a compound having a structure as shown in Formula I or Formula II:

(I)

(II)

wherein $R^1$ is selected from the group consisting of H, $C_{1-12}$-alkyl, $C_{3-8}$-cycloalkyl, $C_{3-8}$-cycloalkyl-$C_{1-12}$-alkyl, amino-$C_{1-12}$alkyl, N—$C_{1-6}$-alkylamino-$C_{1-12}$-alkyl, N,N-di-$C_{1-6}$-akylamino-$C_{1-12}$-alkyl, -continued

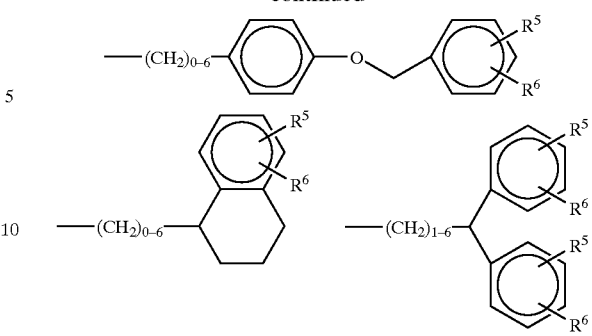

and

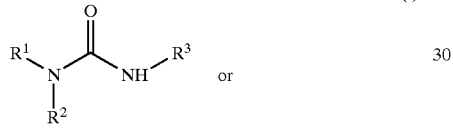

wherein $R^5$ and $R^6$ are independently selected from the group consisting of H, $C_{1-6}$-alkyl, $C_{1-6}$-alkylthio, $C_{1-6}$-alkoxy, fluoro, chloro, bromo, iodo, and nitro; and X is halo;

wherein $R^4$ is selected from the group recited above for $R^1$, and $R^7$ is selected from the group consisting of $H_2N$—$(CH_2)_{1-6}$—   $H_2N$—$(CH_2)_{1-6}$—

$R^2$ and $R^3$ are selected from the group consisting of wherein $R^5$ and $R^6$ are as described above; and pharmaceutically-suitable salts thereof.

2. The method according to claim 1, wherein $R^2$ is

3. The method according to claim 1, wherein $R^2$ is

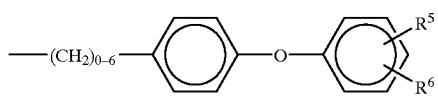

4. The method according to claim 1, wherein $R^2$ is

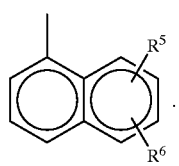

5. The compound according to claim 1, wherein $R^2$ is

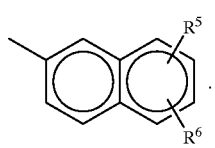

6. The method according to claim 1, which is a method of treating systemic inflammatory response syndrome.

7. The method according to claim 1, having the structure of Formula I.

8. The method according to claim 1, having the structure of Formula II.

9. The method according to claim 1, having the structure of Formula I and further wherein $R^1$ is

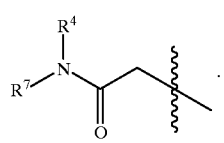

10. The method according to claim 9, wherein $R^7$ is $H_2N-(CH_2)_{1-6}-$.

11. The method according to claim 9, wherein $R^7$ is

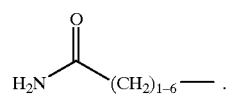

12. The method according to claim 9, wherein $R^7$ is

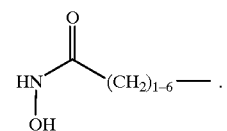

13. The method according to claim 1, wherein $R^1$ is

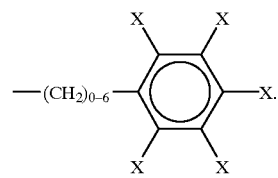

14. The method according to claim 1, wherein $R^1$ is

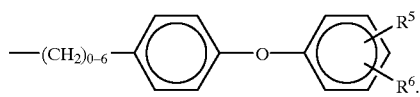

15. The method according to claim 1, wherein $R^1$ is

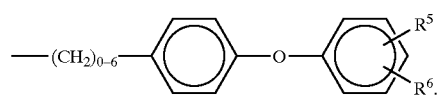

16. The method according to claim 1, wherein $R^1$ is

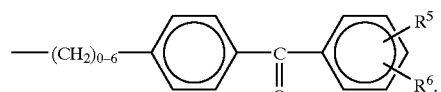

17. The method according to claim 1, wherein $R^1$ is

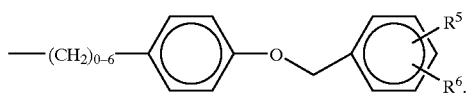

18. The method according to claim 1, wherein $R^1$ is

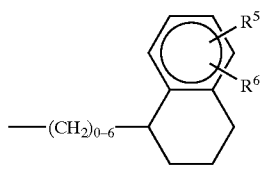

19. The method according to claim 1, wherein $R^1$ is

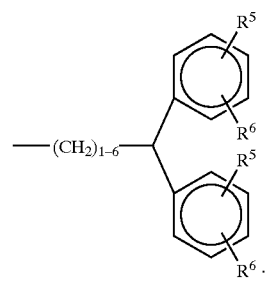

20. The method according to claim 1, wherein $R^3$ is
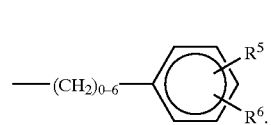
21. The method according to claim 1, wherein $R^3$ is
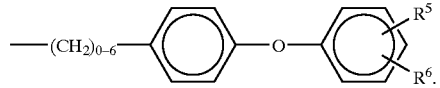
22. The method according to claim 1, wherein $R^3$ is
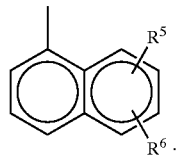
23. The method according to claim 1, wherein $R^3$ is
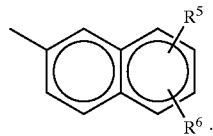
* * * * *